United States Patent
Huys et al.

(10) Patent No.: US 8,452,369 B2
(45) Date of Patent: May 28, 2013

(54) CMOS COMPATIBLE MICRONEEDLE STRUCTURES

(75) Inventors: Roeland Huys, Wilsele (BE); Carmen Bartic, Wilsele (BE); Josine Loo, Leuven (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 1028 days.

(21) Appl. No.: 12/043,285

(22) Filed: Mar. 6, 2008

(65) Prior Publication Data

US 2008/0319298 A1 Dec. 25, 2008

Related U.S. Application Data

(60) Provisional application No. 60/893,699, filed on Mar. 8, 2007.

(51) Int. Cl.
*A61B 5/04* (2006.01)

(52) U.S. Cl.
USPC .......................................... 600/372; 204/409

(58) Field of Classification Search
CPC ....... A61M 37/0015; A61M 2037/0053; A61M 37/00; A61M 2037/0061; A61M 5/3298; A61M 2005/1581
USPC ......... 600/372–385, 393, 395–397; 438/674, 438/675; 257/E21.159; 204/400–435
See application file for complete search history.

(56) References Cited

U.S. PATENT DOCUMENTS 6,334,856 B1 * 1/2002 Allen et al. ................... 604/191

FOREIGN PATENT DOCUMENTS

| EP | 0803702 | 4/1997 |
| WO | WO 95/33504 | * 12/1995 |

OTHER PUBLICATIONS

Lv, Y. et al., "Modeling of Transdermal Drug Delivery with a Microneedle Array", J. Micromech. Microeng., vol. 16, 2492-2501 (2006).

Bergveld, P. et al., "Extracellular Potential Recordings by Means of a Field Effect Transistor Without Gate Metal, Called OSFET", IEEE Transactions on Biomedical Engineering, BME-23(2), 136-144 (Mar. 1976).

Cohen, A. et al., "Depletion Type Floating Gate P-Channel MOS Transistor for Recording Action Potentials Generated by Cultured Neurons", Biosensors and Bioelectronics, vol. 19, 1703-1709 (2004).

Khumpuang, S. et al., "Geometrical Strengthening and Tip-Sharpening of a Microneedle Array Fabricated by X-Ray Lithography", Microsystem Technology, 13(3), 209-214 (2006).

Fromherz, P. et al., "A Neuron-Silicon Junction: A Retzius Cell of the Leech on an Insulated-Gate Field-Effect Transistor", Science, vol. 252, 1290-1293 (1991).

* cited by examiner

*Primary Examiner* — J. Christopher Ball

(74) *Attorney, Agent, or Firm* — McDonnell Boehnen Hulbert & Berghoff LLP

(57) ABSTRACT

The present invention provides an electronic device for sensing and/or actuating, the electronic device comprising at least one microneedle (10) on a substrate (1), each of the microneedles (10) comprising at least one channel (7, 8) surrounded by an insulating layer (6). The present invention also provides a method for making such an electronic device for sensing and/or actuating.

23 Claims, 15 Drawing Sheets

US 8,452,369 B2

CMOS COMPATIBLE MICRONEEDLE STRUCTURES

CROSS-REFERENCE TO RELATED APPLICATIONS

The present application claims priority under 35 U.S.C. §119(e) to U.S. Provisional Patent Application No. 60/893,699, filed Mar. 8, 2007, the entirety of which is incorporated herein by reference.

FIELD OF THE INVENTION

The invention relates to electronic devices for sensing and/or actuating comprising at least one microneedle, and to a method for making such electronic devices.

BACKGROUND OF THE INVENTION

Sensors comprising micro-electrode arrays are used for measuring electrical activity in small networks of neurons. These sensors are often relatively big and only small matrices or arrays of micro-electrodes can be made. Current state-of-the art micro-electrode arrays (MEAs) may contain a maximum of 64 electrodes with a minimal spacing of 100 µm between neighbouring electrodes. The electrodes are often made of flat TiN pads with a maximum diameter of 10 µm. For some applications, smaller spacings, e.g., <10 µm, and a larger number of electrodes, e.g., >60000, may be required.

On-chip single cell recording of electrical activity using field-effect transistors has been demonstrated for large neurons or tissue slices. See P. Bergveld et al., *IEEE Transactions on Biomedical Engineering*, 1976; P. Fromherz et al., *Science*, May 1991; A. Cohen et al, Biosensors and Electronics, January 2004). In the case of mammalian neurons, e.g., hippocampal neurons, the cells are much smaller, which leads to a less efficient electrical coupling. In that case, the cells need to be tightly attached onto the chip surface and make a reliable electrical contact between the cell membrane and the recording device.

Various microneedles have been proposed, but whose size limits their functionality for use in in vitro experiments on small cells. See, e.g., Y.-G. Lv, J. Liu et al., *Journal of Micromechanics and Microengineering*, Vol. 16, No. 11, pp. 2492-2501 (2006); S. Khumpuang et al., *Microsystem Technologies—Micro and Nanosystems—Information Storage and Processing Systems*, Vol. 13, No. 3-4, pp. 209-214 (2007). Further, in EP 0803702, a microneedle apparatus is described in which a probe arm with a microneedle is cantilevered over an electronic circuit. Nevertheless, fixing of the probe arm on the electronic circuit is not straightforward because assembly of micro-fabricated parts is not easy.

SUMMARY OF THE INVENTION

The present invention provides an electronic device for sensing and/or actuating, and a method for making such electronic devices. The electronic device is generally CMOS compatible, and may comprise different types of microneedles on a substrate.

The microneedles in the electronic device may be combined with integrated circuitry and/or microfluidic channels in the substrate on which the device is formed, as well as with extra sensing devices on top of the microneedles.

In a first aspect, the invention provides an electronic device for sensing and/or actuating. The electronic device comprises at least one microneedle on a substrate, each of the microneedles comprising at least one channel surrounded by an insulating layer. An advantage of the electronic device is the fact that the devices can be made by CMOS processing, which allows the combination with CMOS devices in the substrate and devices for sensing and/or actuation purposes on top of the microneedles. Further, the electronic device can be used with small cells, such as neurons.

By "microneedle" is meant, when the substrate is lying in a plane, a structure oriented substantially perpendicular to the plane of the substrate and having a width between about 50 nm and about 10 µm, or between about 100 nm and about 6 µm, and a height of between about 150 nm and about 50 µm.

In a second aspect, the invention provides an electronic device for sensing and/or actuating, the electronic device comprising at least one microneedle on a substrate, each of the microneedles comprising at least one channel surrounded by an insulating layer, wherein at least one of the microneedles comprises a channel that is at least partly filled.

In some embodiments, at least one of the microneedles may comprise at least one channel that is filled with a filling material. In other embodiments, at least one of the microneedles may comprise at least one channel that is hollow, or, in other words, which is not filled. In further embodiments, at least one of the microneedles may comprise at least one channel that is at least partly filled with a filling material.

When being filled with, e.g., a conductive material, such as a metal, the electronic device can be used for electrical stimulation. The conductive material can also be used for read-out purposes or for activating active devices on top of the microneedles. When empty or, in other words, not filled, drugs or chemicals for stimulation can be applied through the hollow or empty channel. In some embodiments, the filling material may a conductive material selected from the group consisting of Cu, Al, and W.

The electronic device may further comprise at least one active or passive element on top of the at least one microneedle. The at least one active or passive element on top of the at least one microneedle may comprise a chip or electronic circuitry.

The insulating layer may have a thickness of between about 50 nm and about 1000 nm. The at least one microneedle may have a diameter between about 100 nm and about 6 µm and a height between about 150 nm and about 50 µm, and an aspect ratio between about 0.5 and about 10.

The electronic device may further comprise a further insulating layer covering at least part of the substrate in between the microneedles. The insulating layer and/or the further insulating layer may comprise at least one material that is an electrically insulating layer or a diffusion barrier layer. The insulating layer and/or the further insulating layer may comprise at least one material selected from the group consisting of $SiO_2$, SiC, and SiN.

The electronic device may furthermore comprise electronic circuitry in the substrate. The electronic device may furthermore comprise at least one microfluidic channel in the substrate.

In a third aspect, the invention provides a method for manufacturing an electronic device for sensing and/or actuating. The method comprises providing on a substrate at least one microneedle comprising at least one channel surrounded by an insulating layer. The providing at least one microneedle may be performed by using CMOS process technology.

An advantage of this method is the fact that CMOS processing allows the combination with CMOS devices in the substrate and devices for sensing and/or actuation purposes on top of the microneedles. CMOS processing also allows one to make small-size needles making it possible to contact small cells, such as neurons. CMOS processing allows one to make arrays of needles (at once, as easy as making one needle on its own, as the same processing steps are used), such that always one needle is correctly placed to contact for example a neuron on the correct contacting location for measurement and/or stimulation (with drugs or electrically).

Providing at least one microneedle may comprise: (a) providing a patterned insulating layer on a substrate, the patterned insulating layer comprising at least one hole extending through the insulating layer down to the substrate; and (b) etching the insulating layer so as to form the insulating layer (6) surrounding at least one cavity.

Providing at least one microneedle may furthermore comprise at least partly filling at least one of the at least one hole with a filling material.

According to other embodiments of the invention, providing at least one microneedle may comprise: (a) providing a patterned layer of filling material, thereby providing studs of filling material on the substrate; (b) providing an insulating material in between and on top of the studs of filling material; and (c) etching the insulating material so as to form the insulating layer surrounding at least one cavity.

The method may further comprise removing at least one of the studs of filling material.

The method may also comprise providing at least one active or passive element on top of at least one microneedle. Providing at least one active or passive element on top of at least one microneedle may be performed by providing a layer of material, a chip, or electronic circuitry on top of the at least one microneedle.

The method may furthermore comprise fabricating electronic circuitry in the substrate. Fabricating electronic circuitry may be performed by using CMOS process technology.

The method may furthermore comprise fabricating at least one microfluidic channel in the substrate.

In a fourth aspect, the invention provides an electronic device formed by the method according to the third aspect of the invention.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
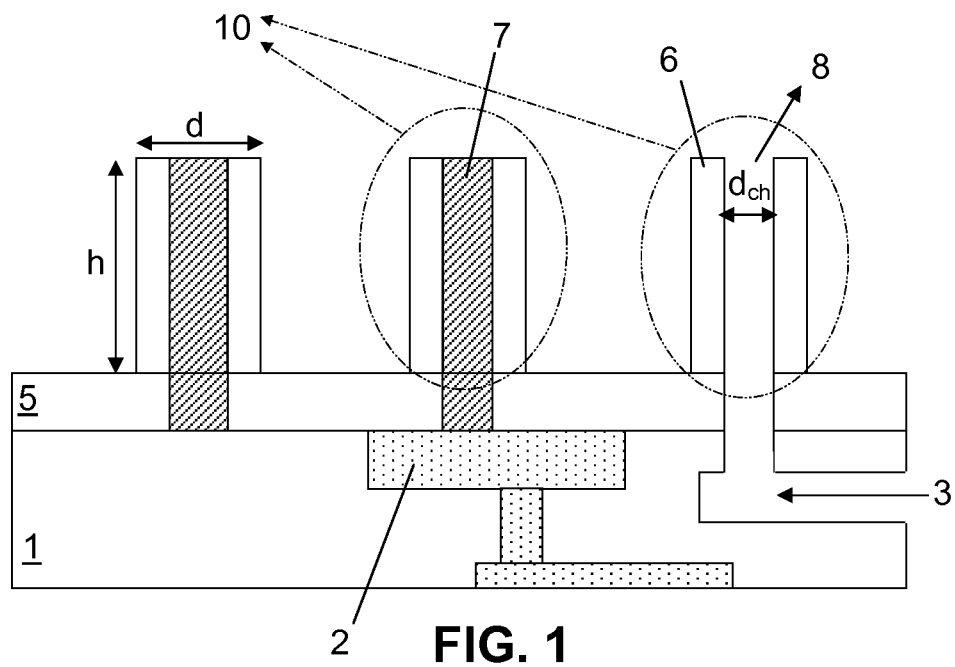
FIG. 1 depicts a cross-sectional view of microneedles on top of a substrate.

In the different figures, the same reference signs refer to the same or analogous elements.

DETAILED DESCRIPTION

The present invention is described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the terms top, bottom, over, under and the like in the description and the claims are used for descriptive purposes and not necessarily for describing relative positions. The terms so used are interchangeable under appropriate circumstances and that the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the technical teaching of the invention, the invention being limited only by the terms of the appended claims.

In many cell-physiological and medical applications, there is a demand to measure biochemical or physical parameters in the close vicinity, e.g., at a distance less than about 5 μm from living cells. This may require experiments which provide measurement of cell-specific molecules, measurement of proteins, measurement of antigens, measurement of ionic displacement, measurement of electrical activity, stimulation by release of drugs or chemicals or stimulation by applying an electrical potential. These experiments can be performed outside the cells in a minimally invasive way, or by penetrating the cell membrane to perform experiments in the cell interior. An example of such experiments, one may stimulate and measure the electrical activity on large quantities of neurons in a minimally invasive way. This may be achieved by integration of actuators and sensors with dimensions comparable to the size of biological cells, for example, neurons, or comparable to the size of parts of the cells, for example, cell organelles or mitochondria. Therefore sensors need to be scaled to a size that approaches the dimensions of one cell or a region-of-interest of a cell. This can be done with, for example, microneedles.

Furthermore, read-out of many sensors simultaneously in an automated way is often required. Therefore, a combination of sensors, for example microneedles and circuitry, for example CMOS circuitry, could be used. It would be beneficial when both the circuitry and the sensors can be made with the same processing techniques.

Developing such combined systems becomes possible by the continuing scaling and integration in the field of microelectronics. CMOS-compatible methods to fabricate microneedle structures with sub-micron dimensions can be developed. Using CMOS compatible processing for fabricating the sensors reduces the risk of problems with the underlying circuitry such as contamination or the use of too high temperatures. Furthermore, the use of lithography and DRIE-etch techniques to create the microneedles facilitates the reproducibility of the shape of the sensors. Thus, matrices of microneedles with sub-micron dimensions or larger can be produced on top of an integrated circuit, e.g., on top of a chip surface using CMOS-compatible processes.

The present invention provides for the use of microneedles or nails, which may be arranged on a substrate randomly or in an array, on top of an integrated circuit, the microneedles having a shaft and isolated electric conductors and/or microfluidic channels inside the shaft. On top of the nails active or passive sensors can be made. Also, a method to produce these nails on top of a substrate is provided.

In general, the proposed technology enables the creation of 3D-topologies with several kinds of materials, or combinations of materials, such as metals, oxides, nitrides, carbides, polymers, organic materials, chemical reactive components, catalysts, biomolecules, enzymes, and other materials used in the field of micromachining or micro-electro-mechanical systems (MEMS). The 3D-topology increases the surface area, which can be advantageous in many applications where a high surface area in a miniaturized scale is required. By using high-density lithography, different electrodes or 3D structures separated from each other with a minimal distance can be created, which can be used in many applications where a small distance between contacts is required, e.g., minimal transport (diffusion) distance of chemical species, or increase of capacitance. This technology can be used in following applications, but is not limited thereto: integrated 3D-capacitors, 3D inter-digitated sensor electrodes, batteries, small-scale fuel cells, microreactors, catalysts systems, small-scaled thermopiles, small-scale heat exchangers, and solar cells.

In one aspect, the present invention provides an electronic device for sensing and/or actuating. The electronic device comprises at least one microneedle on a substrate lying in a plane, each of the microneedles comprising at least one channel surrounded by an insulating layer, also referred to as "shaft," the channel having a longitudinal axis which is directed in a direction substantially perpendicular to the plane of the substrate. The shaft is the material surrounding the at least one channel, formed by the insulating material.

In the description hereinafter, by "microneedle" is meant a structure which is oriented in a direction substantially perpendicular to the plane of the substrate and which has a width between about 50 nm and about 10 μm, or between about 100 nm and about 6 μm, and a height of between about 150 nm and about 50 μm.

The microneedles may have a total width or diameter of between about 50 nm and about 10 μm, or between about 100 nm and about 6 μm, or between about 150 nm and about 5 μm, or between about 500 nm and about 2 μm, or between about 500 nm and about 1500 nm, and a height of between about 150 nm and about 50 μm, or between about 500 nm and about 1500 nm. The lower boundary of dimensions may be determined by limitations of known processes available to form such microneedles.

The device and method according to embodiments of the invention is CMOS compatible. The device may comprise different types of microneedles on one substrate. The microneedles in the electronic device according to embodiments of the invention may be combined with integrated circuitry and/or microfluidic channels in the substrate on which the device is formed, as well as with extra sensing devices on top of the microneedles.

Embodiments of the present invention enable integration of sensors with readout electronics and data processing on a large scale. Also cell stimulation sites can be integrated, e.g. electrical stimulation or controlled release of chemicals through micro-fluidic channels.

Figure 2:
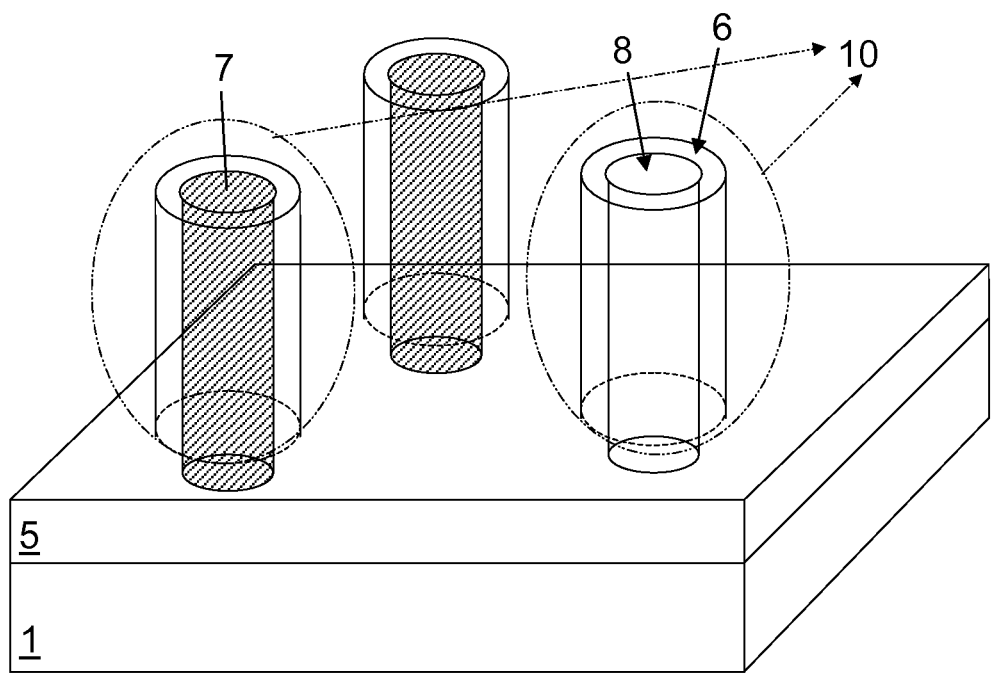
FIG. 2 depicts a three-dimensional view of microneedles on top of a substrate.

FIG. 1 and FIG. 3 to FIG. 5 show cross-sections and FIG. 2 shows a three-dimensional view of implementations of electronic devices according to embodiments of the invention. In the example given in FIG. 1 to FIG. 4, the electronic device comprises three microneedles 10, also referred to as nails, on top of a substrate 1, while in FIG. 5 the electronic device comprises one microneedle 10. It has to be understood that this is only for the ease of explanation and that an electronic device according to embodiments of the invention may comprise any number of microneedles 10 required for a particular application. Microneedles may be provided separately or in groups. When in groups, they may be provided in a regular or in irregular array. When providing arrays of microneedles, always one microneedle may correctly be placed to contact for example a neuron on the correct contacting location for measurement and/or stimulation (with drugs or electrically).

Throughout the description, the terms "microneedles" and "nails" may be used next to each other and are meant to indicate the same entities, e.g., a vertical structure on a substrate or in other words, when the substrate 1 is lying in a plane, a structure having a longitudinal axis oriented in a direction substantially perpendicular to the plane of the substrate 1.

In embodiments of the present invention, the term "substrate" may include any underlying material or materials that may be used, or upon which a device, a circuit or an epitaxial layer may be formed. In other alternative embodiments, this "substrate" may include a semiconductor substrate such as, e.g., a doped silicon, a gallium arsenide (GaAs), a gallium arsenide phosphide (GaAsP), an indium phosphide (InP), a germanium (Ge), or a silicon germanium (SiGe) substrate. The "substrate" may include, for example, an insulating layer such as a $SiO_2$, a $Si_3N_4$, or a sapphire layer in addition to a semiconductor substrate portion. Thus, the term substrate also includes silicon-on-glass and silicon-on-sapphire substrates. The term "substrate" is thus used to define generally the elements for layers that underlie a layer or portions of interest. Also, the "substrate" may be any other base on which a layer is formed, for example a glass or metal layer. The substrate may optionally be planarised. This may be done by for example depositing a planarisation layer of a photoresist, which may for example be an epoxy- or novolac-based polymer, onto the substrate. According to embodiments of the invention, the substrate 1 may be silicon or sapphire.

According to embodiments of the invention, the substrate 1 may comprise electronic circuitry 2 and/or microfluidic channels 3. For example, for stimulation and recording of data, appropriate electronic circuitry 2 can be included in the substrate 1. Other functionality of the electronic circuitry 2 located below the microneedles 10 may be, but is not limited to, matrix addressing circuitry, electrical biasing of electrodes optionally present on top of the microneedle, applying stimulation signals, amplifying recorded signals, transporting data outside the matrix or analog-to-digital conversion.

The electronic circuitry 2 in the substrate 1 may be formed by CMOS technology. The electronic circuitry can be made starting from a CMOS integrated circuit, for example, 0.35 micron technology, 0.25 micron technology, 0.18 micron technology. Also smaller or larger technologies can be used. This may include CMOS front end of line with transistors, contacts and metal layers in the backend of line. Wiring of the circuitry is typically done in the backend of line. For backend metallization for example Al, W, and/or Cu are used. But any other metal known in the art can be used.

The microneedles 10 may be used for sensing and/or actuating purposes. In some embodiments of the invention, the microneedles 10 may be arranged randomly on the substrate 1. In other embodiments of the invention, the microneedles 10 may be arranged in a matrix comprising rows and columns. The microneedles 10 can thus be located in random patterns or in matrices, with a minimal distance between the microneedles 10 of between about 10 nm and about 1 µm, depending on the technology used. In fact, there is no limit on the maximum distance between the microneedles 10, nor on the way the microneedles 10 are patterned.

For other purposes, controlled release of chemicals through micro-fluidic channels may be required. In that case, the substrate 1 may comprise a microfluidic channel 3 which extends up to a hollow channel 8 of at least one microneedle 10 (see further).

The microneedles 10 comprise an insulating layer 6, also called shaft, surrounding at least one channel 8, also referred to as cavity 8, or in other words, the microneedles 10 comprise at least one channel 8 surrounded by an insulating layer 6. The diameter $d_{ch}$ of the channel or cavity 8 of the microneedle 10 may vary between 50 nm and 5 µm, for example between about 500 nm and about 1000 nm.

According to embodiments of the invention, the insulating layer 6 may be adapted to have the function of an electrically insulating layer, (for example SiO, SiN, SiC, and other electrically insulating materials known by a person skilled in the art) or a thermally insulating layer.

According to other embodiments of the invention, the insulating layer 6 may be adapted to have the function of a diffusion barrier for preventing diffusion of material from the inner side of the microneedle 10 through the insulating layer 6 or from outside the microneedle to the inner side of the microneedle or both. For example, when the electronic device is immersed in a liquid, the insulating layer 6 may prevent the liquid to diffuse from outside the microneedle 10 towards the channel 8 of the microneedle 10. The insulating layer 6 may furthermore reduce parasitic capacitance of the electronic device and may, in case of a channel filled with conductive material, improve insulation of the filled channel. For example, in case Cu is used as a conductive material, SiC or SiN may be used as a diffusion barrier. The insulating layer 6 may have a thickness of between 50 nm and 1000 nm, for example between 100 nm and 200 nm. The insulating layer 6 may, for example, comprise silicon oxide ($SiO_2$), silicon carbide (SiC), silicon nitride (SiN), a polymer such as, e.g., polymide, PTFE (poly(tetrafluoroehtylene)), parylene, or any other suitable material that can be used for electrical insulation and/or as a diffusion barrier.

According to embodiments of the invention, the electronic device may comprise at least one microneedle 10 comprising a channel 8 which is hollow, i.e. a channel 8 which is not filled with any solid material.

Figure 3:
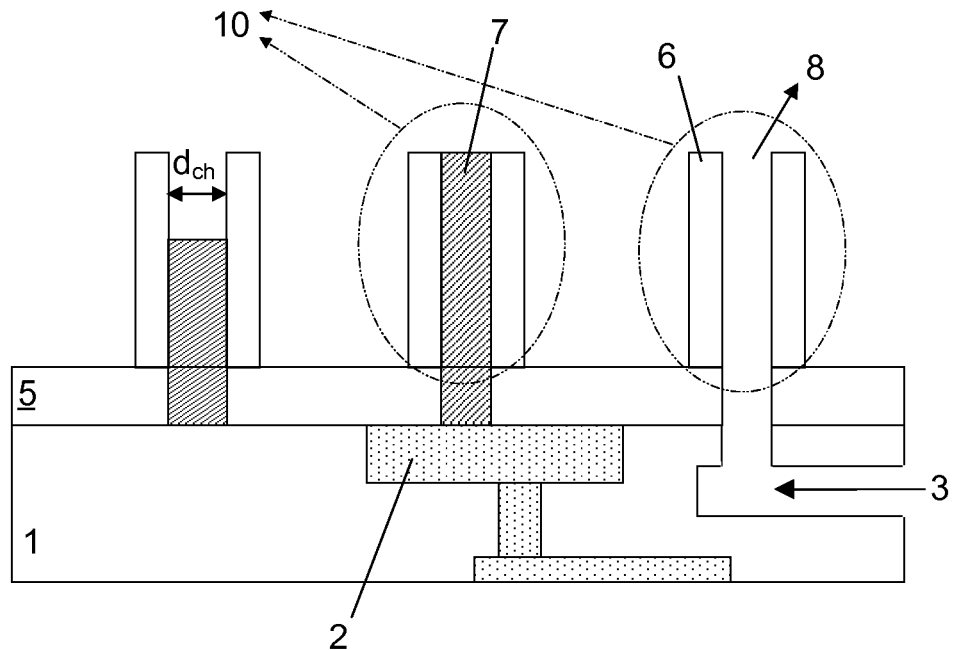
FIG. 3 depicts a cross-sectional view of microneedles on top of a substrate.
Figure 4:
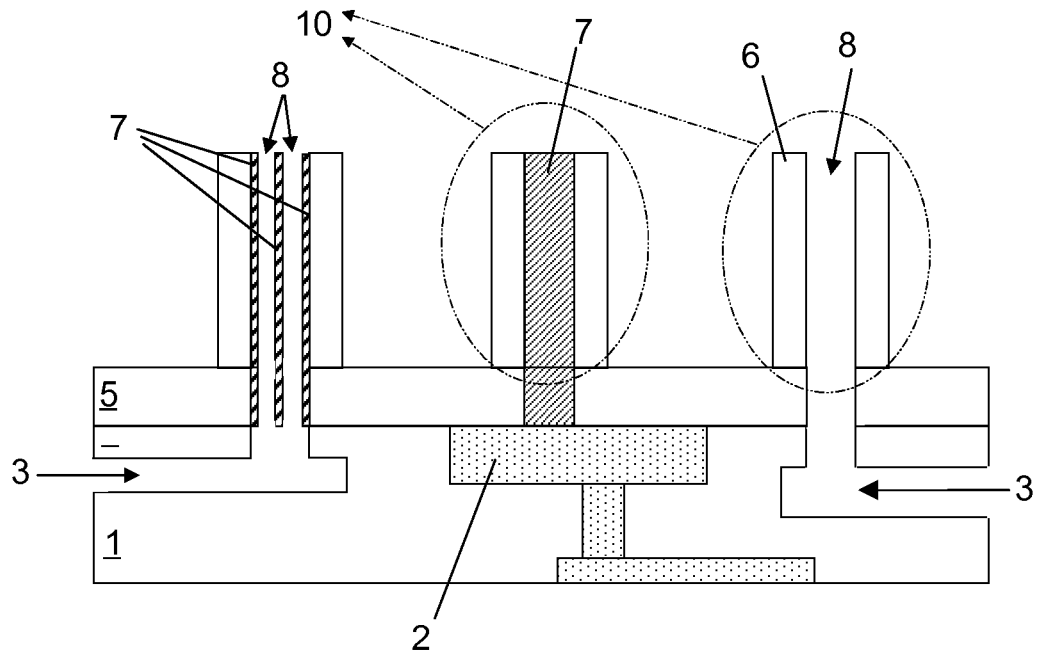
FIG. 4 depicts a cross-sectional view of microneedles on top of a substrate.

In that case, the hollow channel 8 may extend to a microfluidic channel 3 present in the substrate 1 (see FIGS. 1, 3, and 4). According to these or other embodiments of the invention, the electronic device may comprise at least one microneedle 10 comprising a channel 8 which is completely filled with a material, also called "filling material", for example with a conductive material, such as, for example, doped Si, SiGe, Al, Au, Pt, or Cu.

According to these or other embodiments of the invention, the channel 8 may be filled with a biogel, e.g., enzymatic gel, or with a piezoelectric material or a nanostructured material, e.g., a nanowire, may be provided in the channel 8. According to these or still further embodiments of the invention, the electronic device may comprise at least one microneedle 10 comprising a channel 8 which is partly filled with a material, for example with a conductive material. The channel 8 being partly filled can be implemented in two ways. One way may be in case that the microneedle 10 comprises one channel 8. In that case, the channel 8 may be partly filled, i.e. may be filled up to, e.g., about ½ or about ⅓ or about ⅔ of the height of the channel 8, as, for example, in FIG. 3, where the left microneedle 10 is partly filled with a material, e.g., a conductive material.

A second way to implement a partly filled channel 8 is in case the microneedle 10 comprises a plurality of channels 8, and some of the plurality of channels 8 are filled with a material, e.g., conductive material and some of the plurality of channels 8 are hollow, i.e., are not filled, such as, for example, in FIG. 4, where the left microneedle 10 comprises three filled channels 7 and two hollow channels 8. According to any of the above or still further embodiments of the invention, any combination of any number of microneedles comprising a hollow channel 8, microneedles 8 comprising a filled channel and microneedles comprising a plurality of filled channels 7 and hollow channels 8 is disclosed in the invention. For example, the electronic device may comprise a combination of microneedles 10 comprising a completely filled channel 7 and microneedles 10 comprising a hollow channel 8 (see FIG. 1 and FIG. 2). Another example may be an electronic device comprising a combination of microneedles 10 comprising a completely filled channel 7, microneedles 10 comprising a hollow channel 8 and microneedles 10 comprising a channel 8 which is partly filled, e.g. filled for ½ of its height (see FIG. 3). Still another example may be an electronic device comprising a combination of microneedles 10 comprising a completely filled channel 7, microneedles 10 comprising a hollow channel 8 and microneedles 10 comprising a combination of filled channels 7 and hollow channels 8 (see FIG. 4).

The microneedles 10 may have an aspect ratio of between 0.5 and 10, for example between 1 and 10, the aspect ratio of a microneedle 10 being defined by the height h of the microneedle 10 divided by its diameter d (see FIG. 1). The diameter d of the microneedle 10 is defined by the outer diameter of the insulating layer as is indicated in FIG. 1. The height h of the microneedles 10 may vary between 150 nm and 50 μm, for example between 500 nm and 1500 nm.

In some embodiments of the invention, the channel 8 may partly be filled with a conductive material, thereby forming a conducting wire 7 in the channel. The conducting wire 7 may serve for providing electrical contact from the electric circuitry 2 in the substrate 1 through the microneedles 10 towards the outside world, e.g., to external electric circuitry, for, for example, providing electrical stimulation and/or sensing functions to the electronic device. The bottom of the conducting wire 7 makes electrical contact to the electric circuitry 2. The conducting wire 7 may, for example, contact bond pads or other areas of the top metal level of the CMOS backend, but is can also contact areas in other metal levels in the CMOS backend. Typically the top metal of the backend of line is used for contacting the bottom of the microneedles. The metal layers of the CMOS backend form the interconnection between the electronics and the microneedles 10 that can be used as a sensor. The top of the conducting wires 7 can be used for sensing and/or actuation. Hence, the conducting wires 7 may also be referred to as sensors.

The conducting wires 7 may comprise any suitable conductive material that can be used for contacting the electric circuitry 2 in the substrate 1 and which can then serve as a sensor. For compatibility with CMOS technology for example Cu, Al, or W may be used, but any other conductive material that is compatible with respect to temperature budget and/or contamination with CMOS technology may, according to embodiments of the present invention, be used for the conducting wires 7. Other conductive materials that may be used for the conducting wires 7 may be metals such as, e.g., Pt, Au, Al, Cu, Ag, doped Si, or SiGe.

Figure 6:
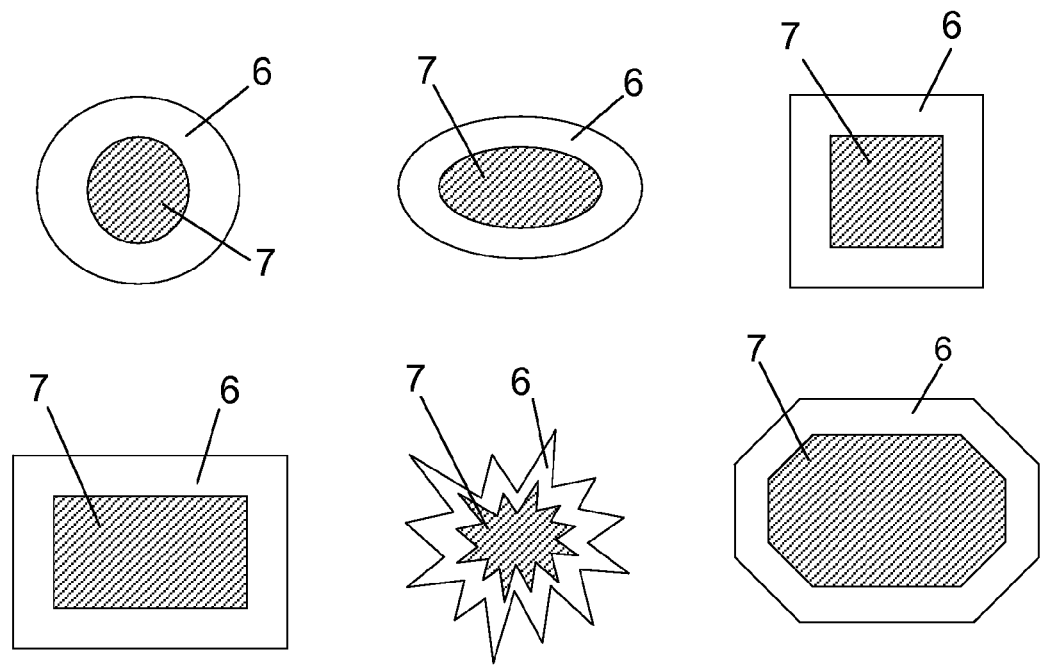
FIG. 6 depicts a top view of microneedles having different shapes.
Figure 7:
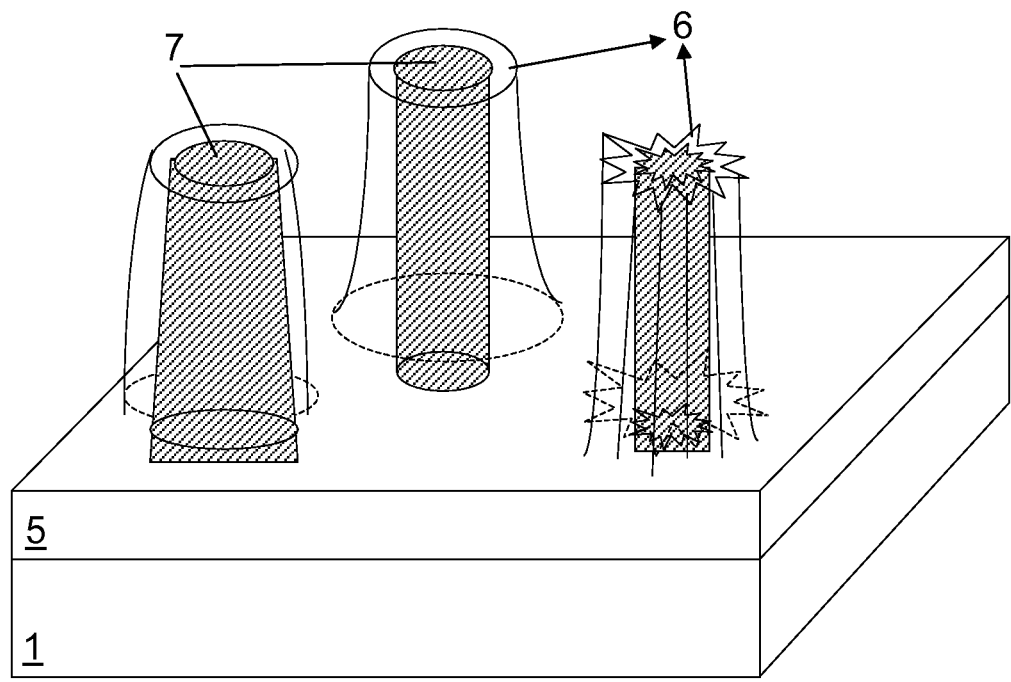
FIG. 7 depicts a three-dimensional view of microneedles having different shapes on top of a substrate.

According to embodiments of the invention, the microneedles 10 may have different shapes (see, e.g., FIG. 6 and FIG. 7). FIG. 6 shows examples of microneedles 10 with different shapes according to embodiments of the invention as seen from the top of the microneedle 10, i.e., from that side of the microneedle 10 opposite to the side that is attached to the substrate 1. A top surface of the microneedle 10 may be circular, oval, square, rectangular, star-shaped, triangular, or may have any other suitable shape. FIG. 7 shows examples of microneedles 10 with different shapes on the substrate 1 of the electronic device. The shape and/or dimensions of the microneedles at their top may be different from the shape and/or dimensions of the microneedles at the substrate. The examples given in FIG. 6 and FIG. 7 are all examples of microneedles 10 comprising an insulating layer 6 surrounding a channel 7 that is filled with a material, e.g. conductive material. It has to be understood that the shapes illustrated in FIG. 6 and FIG. 7 also apply to microneedles 10 comprising an insulating layer 6 surrounding a hollow channel 8, i.e. a channel that is not filled or to microneedles 10 comprising an insulating layer 6 surrounding a channel 8 that is partly filled with a material, e.g. conductive material, as was described above.

An inner and/or an outer side of the insulating layer 6 may be straight, curved, or may have any other suitable shape. The inner and outer side of the insulating layer 6 may make an angle with each other. The shape of the inner and outer side of the second insulating layer 6 may, but does not have to be the same. The shape of the inner and the outer side of the insulating layer 6 may be chosen such that the insulating layer 6 surrounds the channel 8 such that conduction through the conducting wire 7 or fluid transport through the hollow channel is guaranteed.

Between the microneedles 10, on top of the substrate 1, a further insulating layer 5 may be present which at least partly covers the substrate 1. This further insulating layer 5 may be used for electrically insulating and/or protecting the underlying electronic circuitry 2 during further processing of the electronic device. According to embodiments of the invention, the further insulating layer 5 may be adapted to have the function of an electrically insulating layer. Electrically insulating layers may, for example, be $SiO_2$, SiN, SiC, and other materials used in the field. According to other embodiments of the invention, the further insulating layer 5 may be adapted to have the function of a diffusion barrier for preventing diffusion of material from the substrate 1 to the outside world or from the outside world to the substrate 1 or both. A diffusion barrier for example for Cu can be SiN or SiC. According to embodiments of the invention, the further insulating layer 5 may cover only part of the substrate 1. For example, the further insulating layer 5 may cover at least the electronic circuitry present in the substrate 1, but it can also cover the whole substrate 1 in between the microneedles 10. The thickness of the further insulating layer 5 may be between 50 nm and 1000 nm, for example between 300 m and 700 nm or between 400 nm and 600 nm. It has to be noted that this further insulating layer 5 is optional and does, for particular applications, not have to be present. For example, when no electronic circuitry 2 is integrated in the substrate 1, there is no need to insulate the substrate surface, and thus in this case a further insulating layer 5 may not be required. When electronic circuitry is present in the substrate 1 but if the device is used in air or vacuum, which is by itself sufficiently insulating, there is also no need for an additional insulating layer 5. However, if the device is used in non-electrically isolating environments (e.g. liquids, plasmas, ionized gasses), there is a need for an additional insulating layer. Also the use of the device in corrosive environments, environments with a high temperature, etc. also requires the presence of a further insulating layer 5. The further insulating layer 5 may, for example, comprise silicon oxide ($SiO_2$), silicon carbide (SiC), silicon nitride (SiN), a polymer e.g. polyimide, PTFE, Parylene, or any other suitable material that can be used for electrical isolation and/or as a diffusion barrier.

Figure 5:
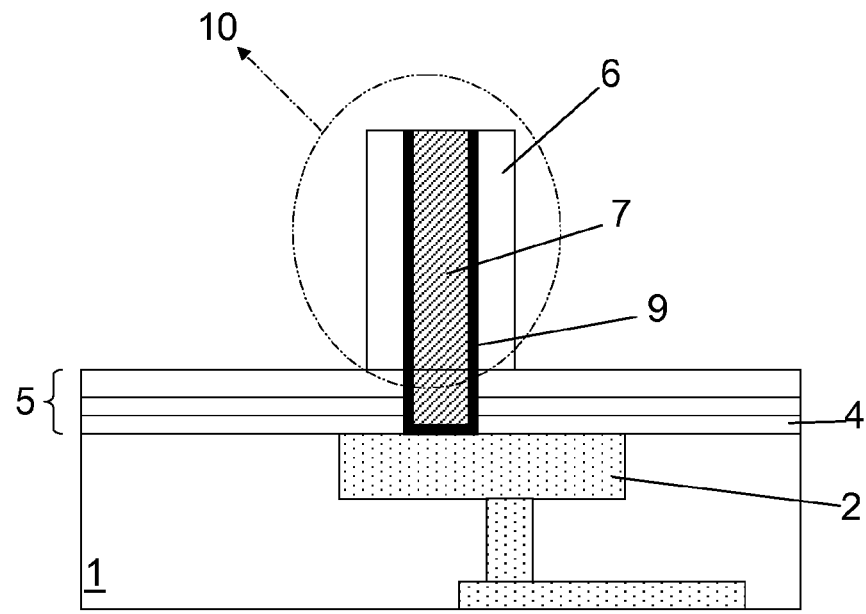
FIG. 5 depicts a cross-sectional view of microneedles on top of a substrate.

The further insulating layer 5 may be made of one material or may be made of different materials, for example of different layers (see FIG. 5). Different layers can be used for example for adhesion purposes, as a barrier layer against diffusion of materials from the microneedles 10 towards the underlying electronic circuitry 2 in the substrate 1. For example, before other layers are provided for the purpose of forming a further insulating layer 5, a first layer 4 may be provided on a major surface of the substrate 1 to reduce stress of the subsequently provided layers, for preventing material to diffuse from the microneedles 10 towards the underlying electronic circuitry 2 in the substrate 1 or vice versa, or for any other reason that requires a particular layer to be provided on the substrate 1 before other insulating layers are provided.

In some embodiments, the further insulating layer 5 and the insulating layer 6 surrounding the channel 8 may be made of a same material. In other embodiments of the invention, the further insulating layer 5 and the insulating layer 6 surrounding the channel 8 may be made of a different material.

In some embodiments, one or more extra layers 9 may be added to the microneedles 10 (see FIG. 5). For example, one or more of diffusion barriers or layers facilitating the provision, e.g., growth, of the conductive material in the channel 8 can be added in between the insulating material of layer 6 and the conductive material and/or at the bottom of the conducting wire 7. These extra layers 9 may, for example, comprise Ti, TiN, Ta, TaN, or any other suitable material known in the field.

In another aspect of the invention, a method is provided for manufacturing an electronic device for sensing and/or actuating. The method comprises forming at least one microneedle 10 comprising at least one channel 8 surrounded by an insulating layer 6 on a substrate 1 lying in a plane, the channel 8 having a longitudinal axis which extends in a direction substantially perpendicular to the plane of the substrate 1.

Forming at least one microneedle 10 may be performed in different ways. Any method known in the art can be used. When using CMOS technology, there are different options, such as damascene processing with metallization, for example Cu metallization, (see FIG. 8(a) to 8(f)) or metal patterning using for example Al metallization (see FIG. 9(a) to 9(h)) for example for making conducting needles. Often higher aspect ratios for the microneedles can be achieved with a damascene process. The two approaches will be described in detail below. It has to be understood that this is not intended to limit the invention in any way and that any other approach known by a person skilled in the art can be used with the method according to embodiments of the invention. The advantage of using CMOS technology is that both the underlying CMOS circuitry 2 present in the substrate 1 and the microneedles 10 can be made with a same technology, using the same tools and thereby thus reducing time and costs required for the processing. Furthermore, CMOS technology allows making very small features with dimensions even in the nm scale, in a reproducible way.

Subsequent steps in damascene processing of microneedles 10 with for example Cu metallization are illustrated in FIG. 8(a) to 8(f). On top of the substrate 1, an insulating layer 14 is provided, e.g. deposited (see FIG. 8(a)). According to embodiments of the invention, the insulating layer 14 can be a single layer, such as $SiO_2$, SiC, or SiN. According to other embodiments, the insulating layer 14 can also be a combination of layers. In case of Cu used as a conductive material a thin SiC layer with a thickness of between 10 nm and 100 nm may first be provided and may later serve as a Cu diffusion barrier and on top of the SiC layer a thick $SiO_2$ layer may then be provided. Next, on top of the insulating layer 14, a thin layer facilitating lithography can be provided, e.g. deposited. The thickness of the insulating layer 14 may correspond to the length of the channel 8 of the microneedle or may preferably be a little bit thicker as some material may be removed at the top of the structure during further processing. The insulating layer 14 may have a thickness of between 10% to 25% larger than the length of the channel 8. The exact thickness of the insulating layer 14 needs to be defined based on the planarising characteristics of the following CMP step and the exact topology of the needles. Hence, strictly spoken the thickness of the insulating layer 14 may be the sum of the length of channel 8 and optionally the amount of material that may be removed during further processing.

Subsequently, holes 11 may be provided, e.g. etched, through the insulating layer 14 extending down to the underlying substrate 1. According to embodiments of the invention, the holes 11 may be provided, e.g. etched down to metal bond pads of electronic circuitry present in the substrate 1 (see FIG. 8(b)). Providing holes 11 in the insulating layer 14 may be performed by any suitable method, e.g. with lithography and dry and/or wet etching, for example deep reactive ion etching (DRIE). As mentioned above (see also FIGS. 6 and 7) with respect to the shape of the channels 8, the holes 11 provided in the insulating layer 14 may have different shapes, for example, seen from a top surface the holes may be circular, cylindrical, square, rectangular, star shaped or may have any other suitable shape in cross-section. All kinds of shapes which allow formation of a channel 8 may be used. The holes 11 may have a diameter of between 50 nm and 5 µm, for example between 500 nm and 1000 nm.

Figure 8:
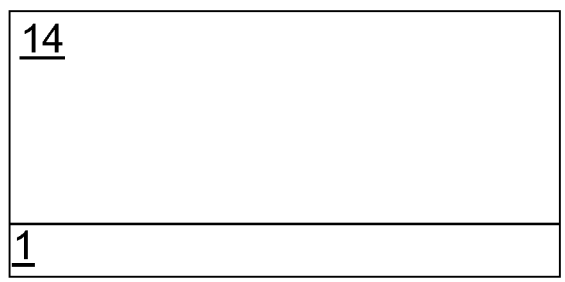
FIGS. 8 (i.e., 8(a) to 8(f)) illustrates different steps in a method for processing of microneedles.
Figure 8B:
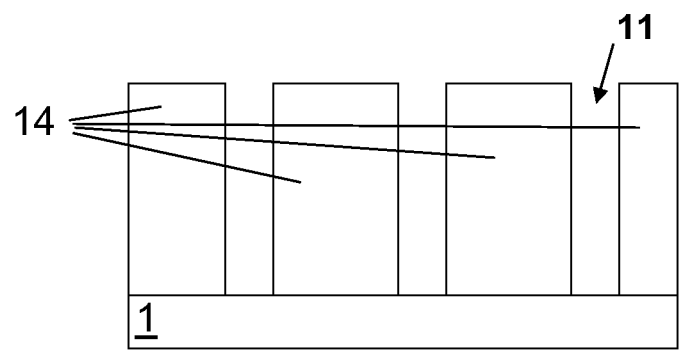
Figure 8C:
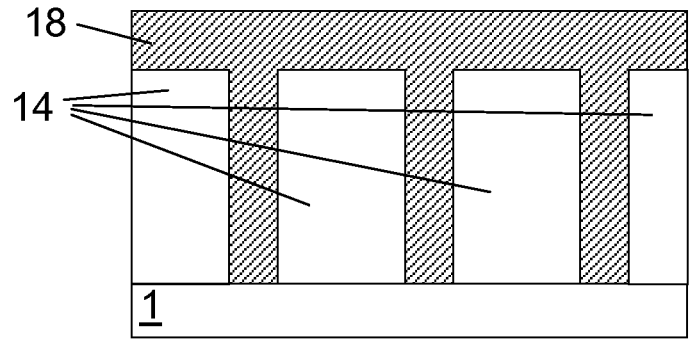

In a next step, the holes 11 may optionally be filled with a filling material 18, e.g., a conductive material such as a metal (see FIG. 8(c)). The conductive material may be Cu or may be any other material that allows filling narrow holes 11. Providing the filling material, e.g. conductive material, may be performed with any suitable technique known by a person skilled in the art such as e.g. electroplating, electroless plating, sputtering or chemical vapour deposition. In some cases a barrier layer may first be deposited on at least a bottom of the holes 11 (not shown in the figures) in order to facilitate filling of the holes 11 and to, later on during further processing and/or use of the electronic device, act as a diffusion barrier for preventing material to diffuse from outside the microneedle 10 to inside the microneedle 10 and/or vice versa. According to embodiments of the invention, also one or more extra layers may be deposited onto the barrier layer prior to filling the holes 11, for example layers for facilitating filling of the holes 11. In case of filling with Cu, the barrier layer may, for example, be combination of Ta/TaN or Ti/TiN. In case electroplating is used for filling the holes with Cu, a Cu electroplating seed layer may first be deposited.

Subsequently, excess of filling material or conductive material may be removed in between the holes using, for example, CMP (chemical-mechanical polishing). During CMP, often a small part of the top of the insulating material 14 may also be removed. After CMP, an insulating layer 14 with holes filled with a material 18 may remain (see FIG. 8(d)).

In the event that only microneedles 10 comprising hollow channels 8 are to be formed, or in other words channels which are not filled, filling of the holes 11 with a filling material 18 is not necessary. Such channels may, for example, serve as microfluidic channels of the electronic device, according to embodiments of the invention. However, hollow channels may also be formed by first filling the holes 11 with a material, e.g., conductive material used as sacrificial metal, and then forming the channel 8 by removing the material from the holes 11 in a later phase by, for example, etching (see further). In case electrical connections between the electronic circuitry in the substrate 1 and the outside world, filling of the holes 11 may be done at this stage.

In the event that microneedles 10 are required which comprise a channel 8 that is only partly filled, the holes 11 may first be filled completely. Next, part of the material the holes 11 are filled with may be removed by, for example, selective etching. According to other embodiments, the holes 11 may just partly be filled with material, e.g. conductive material.

Figure 8D:
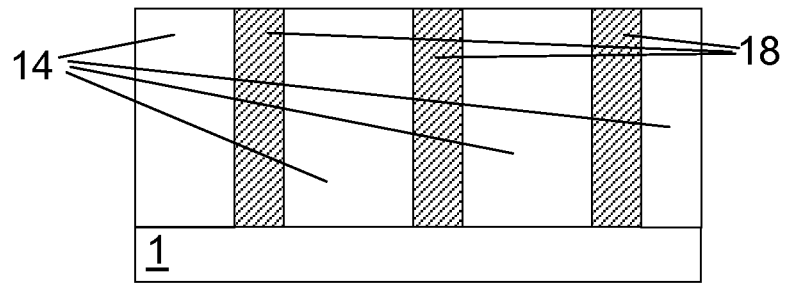
Figure 8E:
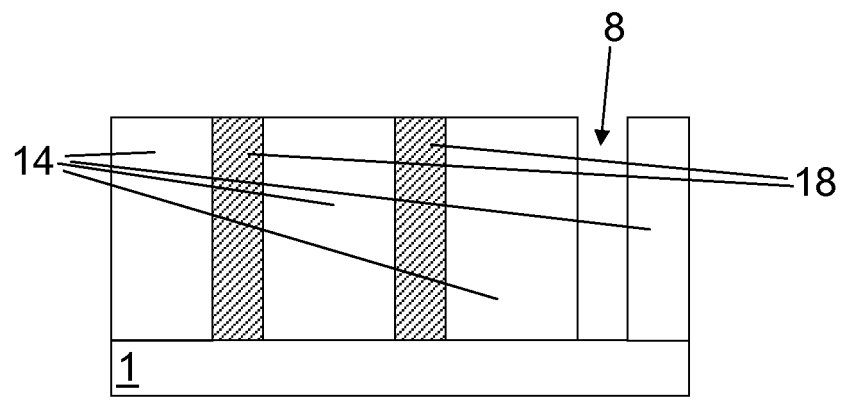

In the event that a combination of hollow channels 8 and filled channels 7 is required, the holes 11 may first be completely filled as described above and the material of the channels of the microneedles 10 which need to be hollow may then be removed from the channels (see FIG. 8(e)). Therefore, a lithography step may be used. The lithography step may comprise covering the substrate 1 with a resist except on the locations where the hollow channels or cavities 8 need to be formed and the sacrificial material, e.g. conductive material can be etched away from the holes. These channels can be created by etching away the sacrificial conductor, creating a hollow channel 8. According to other embodiments, openings in the resist may be provided at locations of the insulating layer 16. Where the insulating layer 16 is not covered with the resist, holes may be etched in the insulating material 16. The technique chosen to form hollow channels 8 may depend on the etching capabilities of the conductive material 17 and/or the insulating material 16.

Figure 8F:
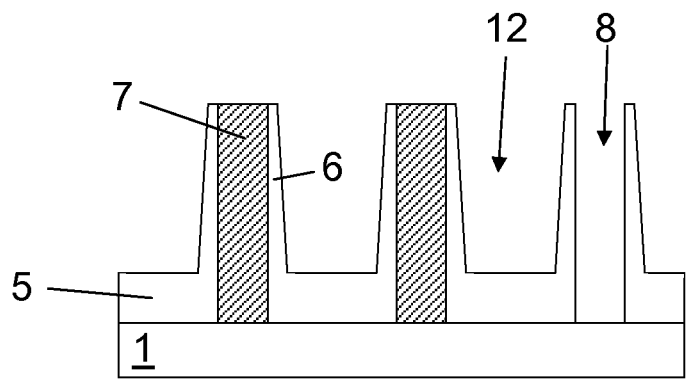

Finally, the microneedles 10 are formed (see FIG. 8(f)). Therefore, dots of resist may be formed on the top of the structure as illustrated in FIG. 8(e) at locations which are not to be removed, i.e., on top of the filled channels and on top of the hollow channels. This may be done by, for example, using lithography. The dots covering the hollow and filled channels may be slightly larger than the diameter of the hollow and filled channels. The extra area of the dots, i.e., the area larger than the diameter of the hollow and filled channels defines the width of the insulating layer 6 surrounding the channels 7, 8. The dots may have a diameter of between 100 nm and 6 µm or between about 600 nm and about 1200 nm.

Subsequently, the insulating layer 6 surrounding the channels 7, 8 may be etched (for example, by DRIE), leaving a thin layer 6 of insulating material of between about 50 nm and about 1000 nm, or between about 100 nm and about 200 nm surrounding the channels 7, 8. The total width or diameter of the microneedles 10 (channels 7, 8+insulating layer 6) may be between about 100 nm and about 6 µm, or between about 600 nm and about 1200 nm.

At the bottom an insulating layer 5 with a thickness of between about 50 nm and about 1000 nm, or between about 300 nm and about 700 nm, or between about 400 nm and about 600 nm remains. The amount of insulating material that is removed in between the microneedles 10 when looking from the top surface defines the length of the microneedles. Thereby, voids 12 are created in between the microneedles 10. The amount of material removed in between the microneedles when looking from the top surface, or else the length or height of the microneedles can be between about 150 nm and about 50 µm, or between about 500 nm and about 1500 nm. The diameter of these microneedles can vary between about 50 nm and about 10 µm, or between about 100 nm and about 6 µm, or between about 150 nm and about 5 µm, or between about 500 nm and about 1500 nm. The aspect ratio (height/diameter ratio) can vary between about 0.5 and about 10.

As already described above, the microneedles 10 may be located in random patterns or in matrices, with a minimal distance in between the microneedles of between about 10 nm and about 1 µm, depending on the technology used. In fact there is no limit on the maximum distance between the microneedles 10, nor on the way the microneedles 10 are patterned.

Control of the etching of the insulating material can be done when knowing the etch rate of the insulating material 14. In that case, the etch time may depend on the amount of material that needs to be removed. Another way to control the amount of material that is etched in between the microneedles 10 may be by introducing an intermediate etch stop layer in the insulating layer 14.

Another approach for making the microneedles 10 is illustrated in FIG. 9(a) to 9(h). This approach uses deposition of a filling material and patterning. This approach may, for example, be used in case of Al, but can also be used for other materials.

Figure 9A:
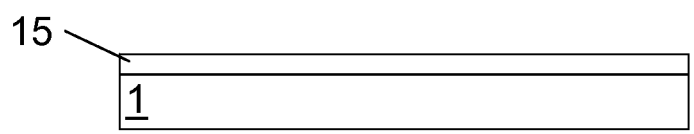
FIGS. 9 (i.e., 9(a) to 9(h)) illustrates different steps in a method for processing of microneedles.
Figure 9B:
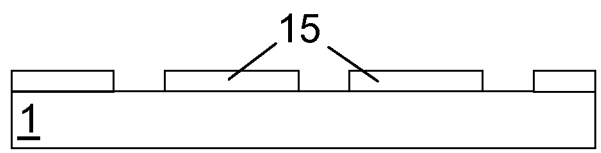

In a first step, on top of a substrate 1 which, for example, comprises a CMOS integrated circuit with transistors, contacts and metal layers (not shown in the figures) an insulating material 15 may be deposited and patterned (see respectively FIGS. 9(a) and 9(b)).

This insulating layer 15 may, for example, be an electrically insulating layer and/or a diffusion barrier. According to embodiments of the invention, the insulating layer 15 may for example be a low-epsilon dielectric such as $SiO_2$, or SiC, or SiN. The insulating layer 15 may, according to embodiments of the invention also comprise a stack comprising different layers. In case of, for example, Cu being used as conductive material, a SiC layer can be included as a diffusion barrier for Cu. This avoids the diffusion of Cu towards underlying transistors of the CMOS integrated circuit. Before depositing the insulating layer 15, according to embodiments of the invention an etch stop layer may be provided, for example SiC when $SiO_2$ is used as an insulating layer 15.

The thickness of the insulating layer 15 may be the thickness that is required for good electrical isolation. The thickness of the insulating layer may be between 50 nm and 1000 nm, for example between about 300 nm and about 700 nm, or between about 400 nm and about 600 nm.

The insulating layer 15 may be patterned so as to provide holes in it. These holes may be used in case of channels 7 filled with a conductive material of the microneedles 10 to be formed need to be able to contact underlying circuitry 2 or in case hollow channels or cavities 5 need to extend to microfluidic channels 3 in the substrate 1. Therefore, the holes need to be provided in the insulating layer 15 at locations where microneedles 10 have to be formed (see FIG. 9(b)). Patterning the insulating layer 15 may be performed by any suitable method, for example, lithography and dry and/or wet etching.

Figure 9C:
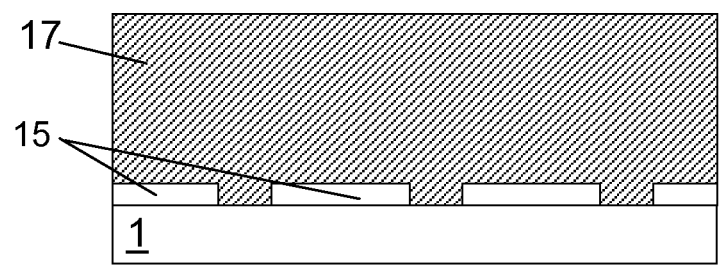
Figure 9D:
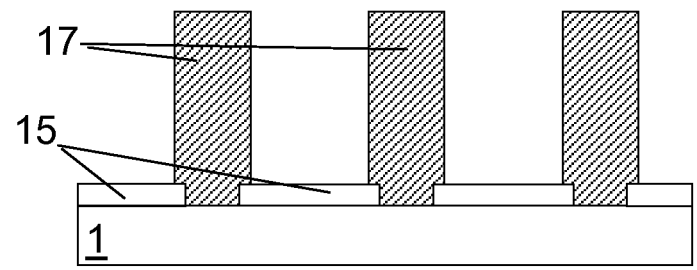
Figure 9E:
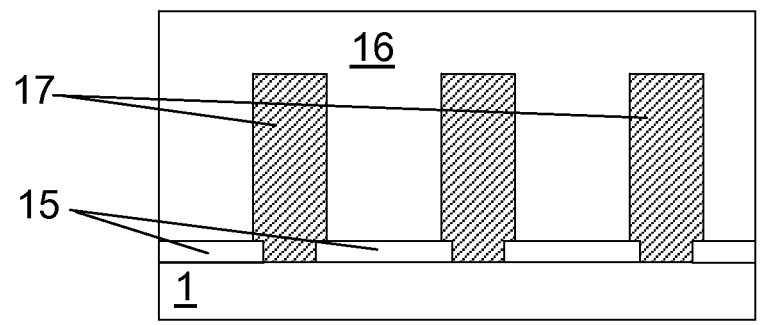
Figure 9F:
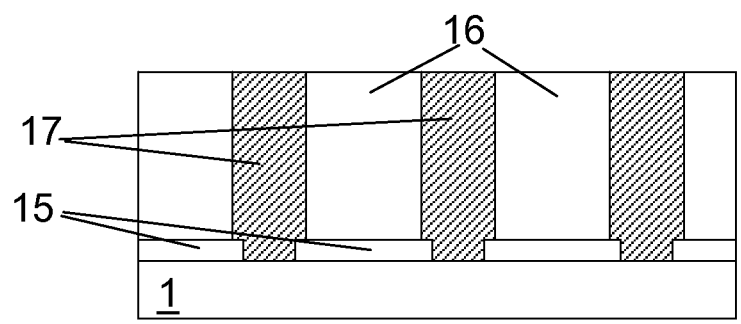
Figure 9G:
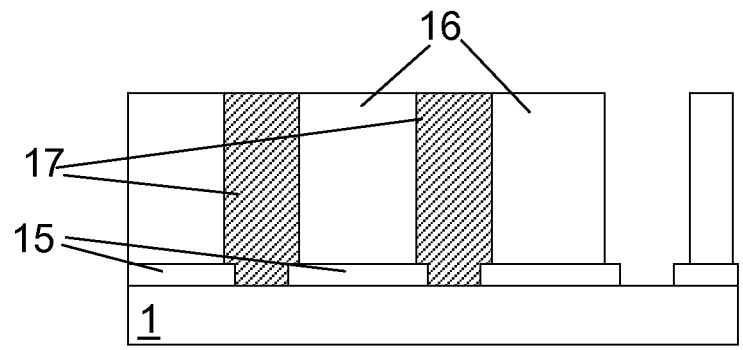
Figure 9H:
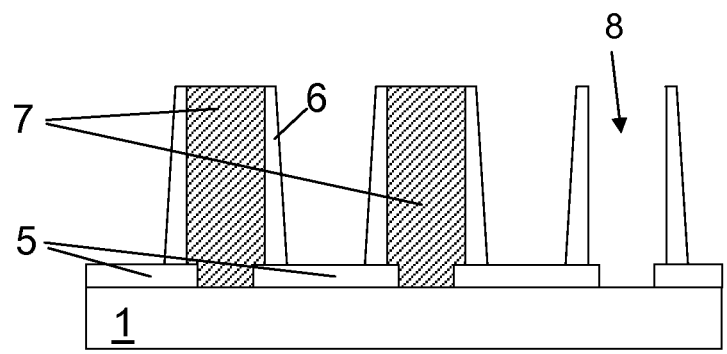

On top of the patterned insulating layer 15 a layer 17 of filling material, for example, conductive material, such as Al, may be provided, e.g., deposited (see FIG. 9(c)). The thickness of the layer 17 of filling material defines the length of the channel 7, 8 of the microneedles 10. The thickness of the layer 17 of filling material may, for example, be between about 150 nm and about 50 μm, or between about 500 nm and about 1500 nm.

In a next step, the layer 17 of filling material may be patterned. This may, for example, be performed by using lithography and dry and/or wet etching. After deposition of the filling material 17, a lithography step using a photo-mask may be performed to make patterns of resist, and a dry and/or wet etching step may then be used to etch away the filling material at the location where no microneedles 10 have to be formed. As a consequence studs of filling material, for example conducting studs, at the locations of the microneedles will be realized (see FIG. 9(*d*)).

According to other embodiments of the invention Instead of first depositing a layer 17 of filling material, local deposition of studs 17 of filling material may be performed through a shadow mask.

Subsequently, gaps that are formed in between the studs 17 by patterning the layer 17 of filling material may be filled with an insulating material 16, such as for example $SiO_2$, $Si_3N_4$, $Ta_2O_5$, or a polymer (see FIG. 9(*e*)). Filling the gaps may be done by any method suitable to deposit a material in high aspect-ratio gaps, such as for example high density plasma chemical vapor deposition (HDP CVD), or spin-on-glass. The insulating material 16 may comprise one material or may comprise different materials. Insulating materials 15 and 16 may comprise a same material or may comprise different materials. Insulating materials 15 and 16 may consist of different materials.

Subsequently, excess of insulating material 16 may be removed in any suitable way. This may be done by removing a top of the insulating material down to the filling material of the studs 17 in order to be able to contact the microneedles 10 from above, i.e. from their top (see FIG. 9(*f*)). Removing excess insulating material 16 and in the mean time possibly flattening a top surface of the insulating layer 16, may be done by any suitable method, for example, etching back or chemical-mechanical polishing (CMP).

In the event that microneedles 10 are required with a filled channel 7, no filling material has to be removed. In case, however, at least one microneedle 10 is required with a hollow channel 8, the filling material may be selectively removed by, for example etching. This may be done at this stage (see FIG. 9(*g*)). Therefore, a lithography step may be used. The lithography may comprise covering the substrate 1 with a resist except on locations where hollow channels or cavities 8 have to be formed. This can be at the location where a stud 17 is present or at locations on the insulating layer 16. Where the insulating layer 16 is not covered with the resist, holes may be etched in the insulating material 16. Where the studs of filling material 17 are not covered with the resist, the filling material may be selectively removed, e.g. etched (see FIG. 9(*g*)). The technique chosen to form hollow channels 8 may depend on the etching capabilities of the filling material 17 and/or the insulating material 16.

Finally, the microneedles 10 are formed (see FIG. 9(*h*)). Therefore, dots of resist may be formed on the top of the structure as illustrated in FIG. 9(*g*) at locations which are not to be removed, i.e. on top of the filled channels and on top of the hollow channels. This may be done by any suitable method, for example by using lithography. The dots covering the hollow and filled channels may be slightly larger than the diameter of the hollow and filled channels. The extra area of the dots, i.e. the area larger than the diameter of the hollow and filled channels defines the width of the insulating layer 6 surrounding the channels 7, 8. The dots may have a diameter of between 100 nm and 6 μm or between 600 nm and 1200 nm.

Subsequently, the insulating layer 6 surrounding the channels 7, 8 may be removed, for example by etching (for example by DRIE), leaving a thin layer 6 of insulating material of between about 50 nm and about 1000 nm, or between about 100 nm and about 200 nm, surrounding the channels 7, 8. The total width or diameter of the microneedles 10 (channels 7, 8+insulating layer 6) may be between about 100 nm and about 6 μm, or between about 600 nm and about 1200 nm.

This insulating material 6 forming the sidewalls of the microneedles 10 may, if the channel of the microneedle 10 is filled, seal the filling material inside the microneedle 10 from the outside world, for example from liquids or other materials. In case of a conductive filling material, it also reduces the parasitic capacitance of the electronic device and improves the electrical insulation of the microneedle 10.

At the bottom an insulating layer 5 with a thickness of between about 50 nm and about 1000 nm, or between about 300 nm and about 700 nm, or between about 400 nm and about 600 nm remains. The amount of insulating material that is removed in between the microneedles 10 when looking from the top surface defines the length of the microneedles. The amount of material removed in between the microneedles when looking from the top surface, or else the length of the microneedles can be between about 150 nm and about 50 μm, or between about 500 nm and about 1500 nm. Thereby, voids between the microneedles 10 may be created. The microneedles 10 may be located in random patterns or matrices, with a minimal distance between the microneedles 10 of between about 10 nm and about 1 μm, depending on the technology used. In fact there is no limit on the maximum distance between the nails, nor on the way the nails are patterned.

Control of the etching of the insulating material can be done when knowing the etch rate of the insulating material 15, 16. In that case, the etch time may depend on the amount of material that needs to be removed. Another way to control the amount of material that is etched in between the microneedles 10 may be by introducing an intermediate etch stop layer in the insulating layers 15, 16. Still another option is to select different insulating materials for layers 15 and 16 such that insulating material 15 acts as an etch stop layer for the chemistry that is used for etching insulating material 16.

Finishing of the electronic device, which may be, e.g., a sensor or an actuator, can be done in different ways, depending on the application. Extra components can be added on top of the microneedle 10. Hereinafter some examples will be discussed on how microneedles 10 can be finished. These examples are intended for illustration purposes only and are not intended to limit the invention in any way. In the examples discussed hereinafter, the different parts may, even if not mentioned, comprise same materials as described in the embodiments above and may be formed using same techniques as described earlier. Any combination of materials and techniques used and described in the different embodiments above may be combined in order to make electronic devices and microneedles 10 which are described hereinafter. Furthermore, parts present in any of the electronic devices as described before or hereinafter which are the same in further described electronic devices may not always be discussed anymore. It has to be understood that, as illustrated in the figures, these parts have a same function and are formed of a same or similar material as was described for earlier discussed electronic devices according to embodiments of the invention.

In FIG. 10(a) to 10(d) examples of different implementations of electronic devices according to embodiments of the invention and examples of different ways of microneedle finishing are illustrated.

Figure 10A:
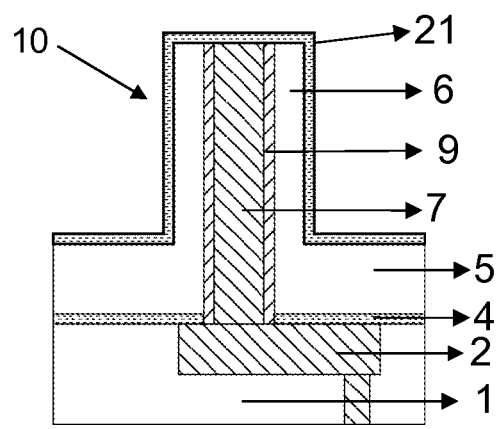
FIGS. 10 (i.e., 10(a) to 10(d)) illustrates different ways of finishing microneedles.

A first example is given in FIG. 10(a). In this example given, the microneedle 10 may comprise an insulating layer 6 surrounding a filled channel 7. The conductive material of the filled channel 7 may be in contact, e.g. electrical contact with underlying electronic circuitry 2 which is provided in the substrate 1. Often the conductive material may be in contact with a bonding pad of a top metal level, which may for example comprise Al or Cu, of the backend of line, or in other words with wiring towards the underlying electronic circuitry 2. In the example given, an additional layer 4 may be present in between insulating layer 5 and the substrate 1. This may, for example, be a diffusion barrier layer. The diffusion barrier layer may, e.g. in case the conductive material in the filled channel 7 is Cu, comprise 50 nm SiC as a diffusion barrier against Cu. According to other embodiments of the invention, this additional layer 4 may be an etch stop layer. The etch stop layer may, e.g. in case insulating layer 5 comprise an oxide, for example be SiC. Insulating layer 5 may, as already discussed above, be an electrically insulating layer or a dielectric material to reduce parasitic capacitances between neighbouring filled channels 7, also referred to as conductors, or between the filled channels 7 and the surrounding atmosphere, for example gas or liquid. It also protects and shields the conducting material of the filled channel 7 from surrounding atmosphere, for example gas or liquid.

Furthermore, the microneedle 10 illustrated in FIG. 10(a) may comprise an extra layer 9 in between the conductive material and the insulating layer 6. This extra layer 9 may, for example have the function of a diffusion barrier for preventing diffusion from outside the microneedle 10 to the inside of the microneedle 10 and/or vice versa or may have the function of facilitating deposition of the conductive material in the channel, depending on the technique used to form the microneedles 10 (see earlier). For example, in case Cu is used as a conductive material, the extra layer 9 may comprise a combination of TaN and Ta.

The electronic device illustrated in FIG. 10(a) may be used as a capacitive sensor, a battery or organic optical devices, organic solar cells, chemical sensors, biosensors. Therefore, it may comprise an additional layer 21 on top of the structure.

For a capacitive sensor, the additional layer 21 may be an insulating layer and may, for example, be formed by deposition of a thin insulating layer with a thickness of between about 10 nm and about 200 nm at a last stage of the manufacturing process, e.g., after the microneedles 10 have been formed. By depositing an insulating layer 21, which may for example comprise about 100 nm of $Ta_2O_5$ or a thin oxide layer or a high-k dielectric, such as $Ta_2O_5$, $HfO_2$, $Ti_2O$, SiC, polymers, or biomolecules, the microneedle 10 may become a passive electrode. The thin insulating layer 21 may form a barrier between the conductive material 7 of the microneedle 10 and the outside world, for example a liquid. Hence, the electronic device illustrated in FIG. 10(a) may serve as a capacitive sensor.

For a battery, the additional layer 21 may comprise a conductive material or a combination of conductive materials, such as, e.g., Au, Pt, Ti, Al, Cu, Zn, and/or C. For example, an electronic device comprising microneedles 10 having a channel 7 filled with carbon, covered with a layer 21 of conductive material and brought in contact with a suitable electrolyte can be used as a 3D Li-ion microbattery.

For organic optical devices, organic solar cells, chemical sensors or biosensors the additional layer 21 may comprise a polymer.

For still further applications, the additional layer 21 may comprise a semiconductive material.

Figure 10B:
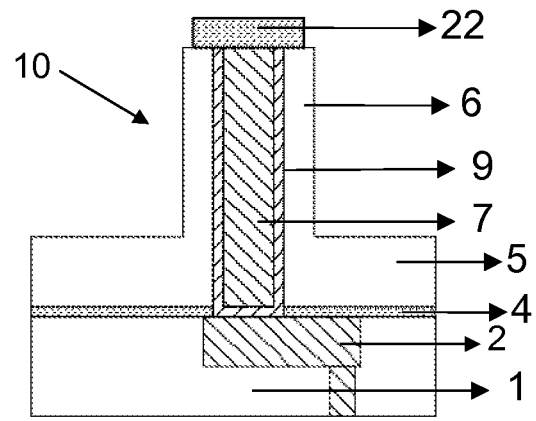

A second example of an electronic device according to embodiments of the invention is illustrated in FIG. 10(b). In this example given, the microneedle 10 may comprise an insulating layer 6 surrounding a filled channel 7. The electronic device illustrated in FIG. 10(b) may function as a passive sensor or passive electrode. In the example given, the microneedle 10 comprises on a top surface a dot 22 of material, e.g. a noble metal or a semiconductor material. The dot 22 may be formed by, for example, depositing the material through a shadow mask or by providing a layer of the material and patterning the material using, e.g., lift-off techniques. Also, lithography techniques combined with dry and/or wet etching may be used for this purpose. In case of lithography, the top surface on which the lithography has to be performed needs to be substantially flat to have sufficient depth of focus for lithography. Provision of the dots 22 may, for example, be performed before final formation of the microneedles 10 by etching the insulating material as was illustrated in FIG. 8(d) or 8(e) or FIG. 9(f) or 9(g) depending on the technique used to form the microneedles 10.

In some embodiments, the dots 22 may comprise a noble metal such as, for example, Au or Pt. Au may, for example, be deposited by electroplating or electroless (chemical) plating. Pt may, for example, be deposited by electroless (chemical) plating. In case of a noble metal, the dot 22 can be used as an electrical sensor or stimulator for measuring activity of, or stimulating electrically active cells, such as e.g. neurons.

In other embodiments of the invention, the dots 22 may comprise a semiconductor material.

In further embodiments, the dots 22 may comprise an insulating material, for example a thin oxide layer or a high-k dielectric, such as, e.g., $Ta_2O_5$, $HfO_2$, $Ti_2O$, SiC, a polymer, or a biomolecule, for use as a capacitive sensor.

According to still further embodiments of the invention, the dots 22 may also comprise a polymer for use as organic optical devices, organic solar cells, chemical sensors or biosensors.

The dot 22 may be bio-functionalized. In that way, the electronic device may be used as a sensor for protein detection, antigen detection, DNA detection, microparticle or nanoparticle detection, or detection of any other type of molecule. The sensor may also be used in other types of measurements and experiments, such as e.g. amperometric measurements or impedance-spectroscopy measurements.

An active sensor may be formed by depositing a Si layer and creating doped areas and interconnect patterns. Similar as described above, for lithography, the top surface on which the lithography has to be performed needs to be substantially flat, as represented in FIG. 8(d) or 8(e) or in FIG. 9(f) or 9(g). The simplest implementation of an active sensor may be an ISFET (ions-sensitive field effect transistor) made of a p-silicon bulk, n-doped source and drain areas, contacts to connect to the vias through the microneedle 10, and a thin oxide on top. The sensor may also be an organic based ISFET.

Figure 10C:
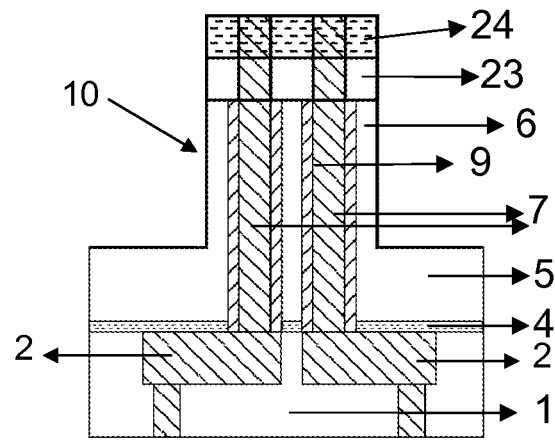

A third example of an electronic device according to embodiments of the invention is illustrated in FIG. 10(c). In this example given, the microneedle 10 may comprise an insulating layer 6 surrounding a partly filled channel thereby forming two filled channels 7 isolated from each other by an insulating material. This may also be referred to as a microneedle 10 comprising multiple conductors 7 isolated from each other by an insulating material. As can be seen form FIG.

10(c) each of the filled channels or conductors 7 may be connected with a different electronic circuitry 2 present in the substrate 1. According to some embodiments, however, all filled channels or conductors 7 may connected to a same electronic circuitry 2 present in the substrate 1 (not shown in the figures). On top of the microneedle 10 at least one extra layer, electronic circuitry, or a chip may be present. In some embodiments of the invention, the devices on top of the needles in FIGS. 10(c) and 10(d) can be fabricated after steps (d) or (e) in FIG. 8 or steps (f) or (g) in FIG. 9. In this approach, first a protecting insulator 23 is deposited, followed by the deposition of a semiconductor layer 24, e.g. silicon. Then holes, in the example given two holes may be etched through the semiconductor layer 24 and the insulation layer 23. Subsequently, the holes can be filled with a filling material. This filling material can be a conducting material. The excess of filling material can be removed with for example CMP. Finally an etching step is performed so as to realise the needles.

Figure 10D:
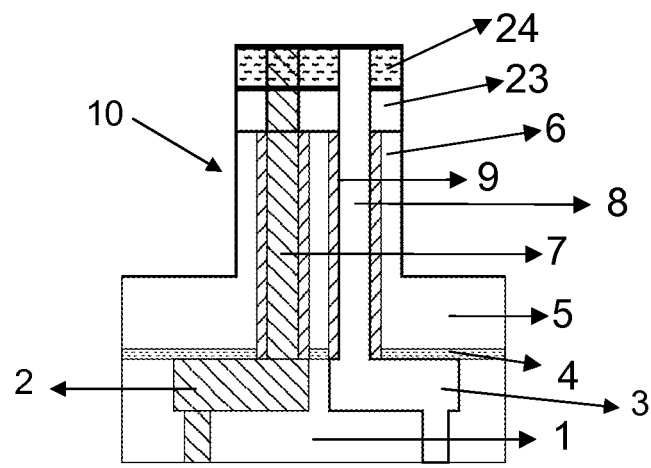

In other embodiments, it may also be possible to fabricate the devices represented in FIGS. 10(c) and 10(d) on top of the needles after the step as illustrated in FIG. 8(a). In that case, first layers 23 and 24 can be deposited onto the insulating layer 14. Then holes may be etched through the layers 24 and 23, and through insulating layers 5 and 6 underneath. The holes are filled with a conducting material followed by removal of excess of conductive material by e.g. CMP as described in FIGS. 6(c), and (d). Finally an etching step may be performed so as to realise the needles. According to still further embodiments, electronic devices which comprise a sensor may be formed on top of the needles. This may be done as follows. First a layer of semiconductor material such as e.g. silicon, may be deposited. Filled channels 8 through the silicon can be made by a patterned implantation of a p-type doping material such as e.g. boron. Active parts of the sensor can be made by patterning p- and n-doped regions on top of the filled channels, thus forming semiconductor circuits. On top of this, a sensor can be made by depositing an electrode comprising, for example, Au, TiN, Pt, or any other appropriate metal, or by depositing a thin oxide layer such as e.g. $SiO_2$ or a high-k dielectric, such as, e.g., $Ta_2O_5$, $HfO_2$, $Ti_2O$, SiC, a polymer, or a biomolecule, for use as a capacitive sensor. In general a chip or electronic circuitry on top of the microneedle 10 can be made as follows. A chip may be formed using the following processing steps: patterning for doped regions, providing metal layers and circuits. Many types of active sensors can be formed, such as, e.g., ISFETs, photoreceptors, or other chips. Subsequently, the chip outline around the microneedle 10 may be etched to isolate the chips on top of the microneedle 10. Finally, finishing of the active electrode depends on the type of active sensor required. In case of an ISFET, it may, for example, be required to add a layer of a high-k dielectric material.

A fourth example of an electronic device according to embodiments of the invention is illustrated in FIG. 10(d). In this example given, the microneedle 10 may comprise an insulating layer 6 surrounding a filled channel 7 and a hollow channel 8 isolated from each other by an isolating material. The hollow channel 8 may function as a microfluidic channel. The filled channel 7 may be connected to electronic circuitry 2 present in the substrate 1 and the hollow channel 8 may be connected with a microfluidic channel 3 present in the substrate 1. The filled channel 7 and the hollow channel 8 may be formed by any technique as described above and may be formed before creating a chip or electronic circuitry on top of the microneedle 10. This can be done performed after step (d) in FIG. 8 or step (f) in FIG. 9, before creating a chip or a sensor or any other electronic circuitry on top of the microneedle 10.

According to the example given in FIG. 10(d), on top of the microneedle 10 a sensor, e.g. pH sensor, ISFET or biosensor, may be formed to, for example, detect an amount of liquid released by a microfluidic channel 7 of the device. This may, for example, be used to detect chemical reactions in close vicinity of the microneedle 10 between the released liquid and a medium outside the microneedle 10, to detect biomolecules released by a cell with the microneedle 10 inserted into the cell, to measure and quantify an amount of liquid released by the microfluidic channel 7 of the device, or to perform a micro-dialysis method, which requires an inlet and an outlet.

The electronic device illustrated in FIG. 10(d) may thus function as a microfluidic chip. Examples of microfluidic chips may be electrophoresis-driven microfluidic actuators (micro-pumps to pump in or out the liquid), piezo-electric driven actuators or MEMS based valves.

It is possible to transport nanoparticles through the microfluidic channels 3, 8. For example, a nanoparticle sensor could be added, e.g. of an electrostatic type. Furthermore, nanoparticle actuators can be added on top of the microneedle 10 to drive the nanoparticles. This can be used to inject nanoparticles inside a cell. The nanoparticles can be bio-functionalized to bind specific molecules, and the nanoparticles can afterwards be detected using the sensor on top of the microneedle 10, or even be transported back outside the cell to analyze it using the electronic circuitry below the microneedles 10, i.e. the electronic circuitry 2 in the substrate 1. This could also be performed in a micro-dialysis type of approach.

It has to be noted that, although the presence of electronic circuitry or a chip on top of the microneedle 10 is only illustrated for the electronic devices of FIGS. 10(c) and 10(d) in combination with a microneedle 10 having a channel that is partly filled, according to embodiments of the invention electronic circuitry or a chip may also be provided on top of microneedles 10 having any configuration as described in the above discussed embodiments.

Hereinafter some experimental examples will be described. It has to be understood that these are only for illustration purposes and are not intended to limit the invention in any way.

Example 1

Microneedles 10 with a width of approximately 250 nm and a height of 1 μm were produced using a Cu damascene approach. The microneedles 10 were further oxidized or electroplated with a noble metal to prevent Cu-induced cytotoxicity.

Cu microneedles 10 comprising a $SiO_2$ isolation layer 6 have been made using CMOS processing techniques. The different processing steps are described below. The steps refer to the steps as presented in FIG. 11.

Figure 11A:
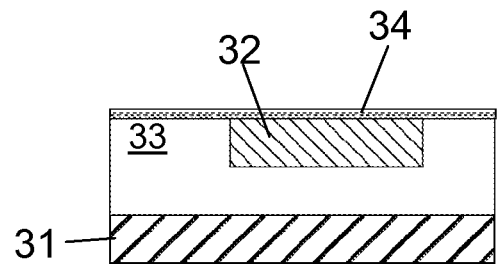
FIGS. 11 (i.e., 11(a) to 11(h)) illustrates subsequent process steps for making microneedles.

First (see FIG. 11(a)) 8" Si wafers 31 with a Cu damascene metal pattern 32 in a $SiO_2$ dielectric 33 were created. The pads in this Cu damascene metal layer 32 are acting as base on which the microneedles 10 will be formed. On top a layer 34 of 50 nm SiC was deposited. The SiC layer 34 will act as a diffusion barrier between the Cu and the underlying electronic circuitry 32 (Cu diffusing in the liquid is toxic for the cells) and is also used as an etch stop layer.

Figure 11B:
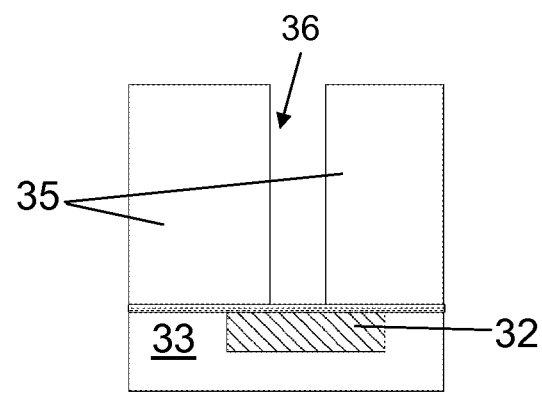
Figure 11C:
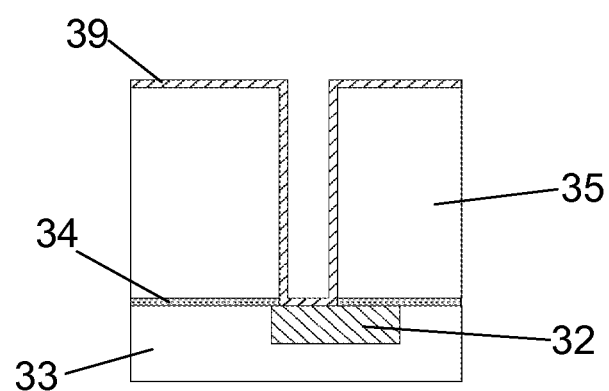
Figure 11D:
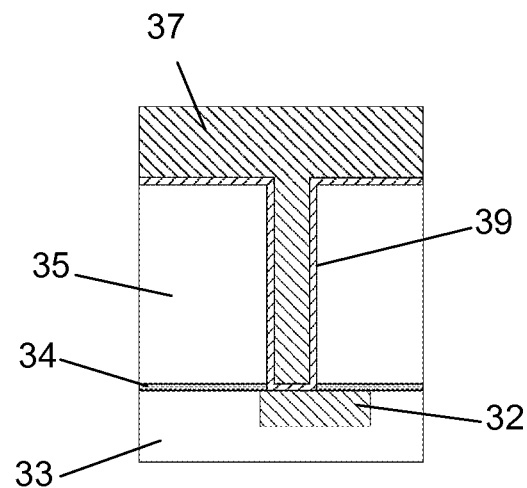

Subsequently, a layer 35 of oxide was deposited (see FIG. 11(b)). The layer 35 of oxide had a thickness of 1.4 μm. A lithographic step was then performed, with used a dark-field mask with holes of 250 nm to 1000 nm to form holes 36 in the oxide layer 35. The holes 36 were etched with DRIE etch through the oxide down to the SiC layer 34 which acts as an etch stop layer. In another etching step, the SiC layer 34 was then removed.

Next, a TaN/Ta barrier layer 39 of 10 nm TaN and 5 nm Ta was deposited (see FIG. 10(c)). The TaN/Ta barrier layer 39 will acts as a diffusion barrier for preventing Cu diffusion. Subsequently (see FIG. 11(d)), the holes 36 were filled with Cu 37 by Cu plating. This was followed by CMP step in order to remove the excess Cu on the oxide layer 35 in between the holes 36 (see FIG. 11(e)).

Subsequently (see FIG. 11(f)) a lithographic step was performed using a bright-field mask with dots 40 with dimensions, e.g. diameters ranging from 500 nm to 1.25 µm, thereby covering an area slightly larger than the holes 36, as was described earlier (see FIG. 11(g)). This was followed by a DRIE etch, which was timed in such a way that 1 µm of oxide was removed. As a result, a $SiO_2$ layer 36 with a thickness of 125 nm remains to form sidewalls of the microneedles 10. This serves for two major purposes: sealing the Cu inside the microneedles 10 from contaminants from the outside world (for example liquids) and reduction of parasitic capacitance thereby improving the isolation. Finishing the sensor as a passive electrode was done by depositing a 100 nm layer 38 of $Ta_2O_5$ (see FIG. 11(h)).

The electronic device formed serves as a capacitive sensor, and prevents the Cu inside the microneedles 10 to come in contact with the environment (such as liquids).

Figure 12A:
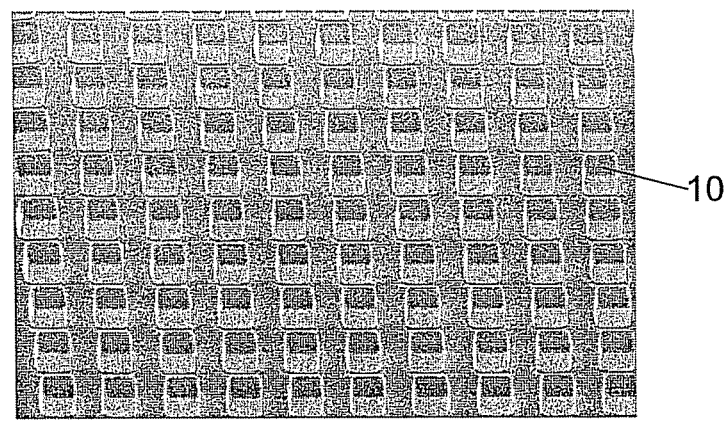
FIGS. 12 (i.e., 12(a) to 12(c)) shows SEM pictures of microneedles covered with a 100 nm thick layer of $Ta_2O_5$.
Figure 12B:
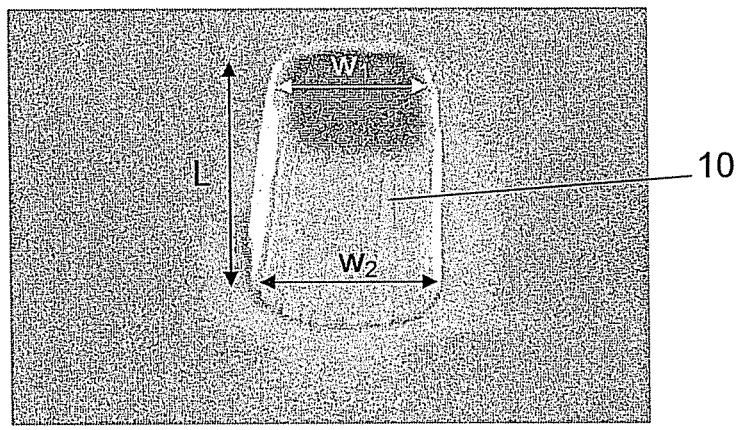
Figure 12C:
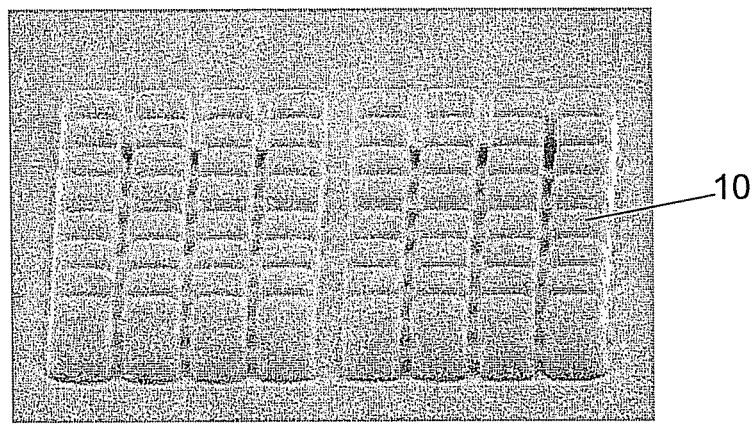

FIGS. 12(a), 12(b) and 12(c) show SEM pictures of microneedles 10 formed in the experiment described above. Various types of microneedles 10 with several dimensions were made. In FIG. 12(a) an array of microneedles 10 is shown obtained with a method according to the present experiment. FIG. 12(b) shows one microneedle 10 from the array of microneedles 10 shown in FIG. 12(a). The microneedle 10 shown FIG. 12 (b) has a width $w_1$ of 500 nm at the top and a width $w_2$ of 550 nm at the bottom. The length L is 1050 nm. Furthermore, at the sidewalls 100 nm of $Ta_2O_5$ can be observed. In FIG. 12(c) another array of microneedles 10 is shown obtained with a same method according to the present experiment.

As can be seen from FIGS. 12(a) and 12(c) the microneedles 10 may be provided in a matrix comprising logically organised columns and rows.

Figure 11E:
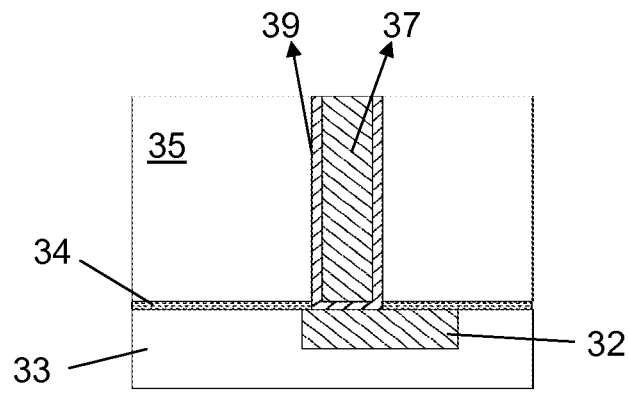
Figure 11F:
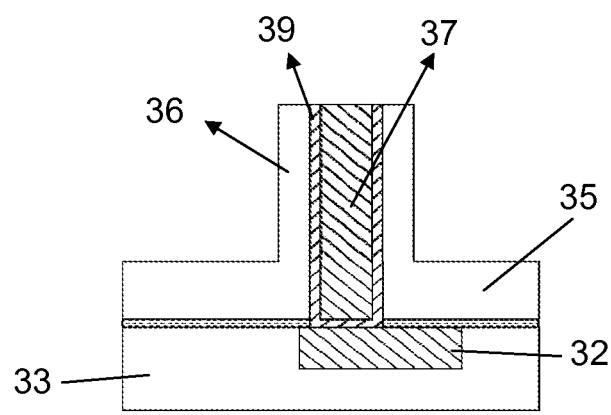
Figure 11G:
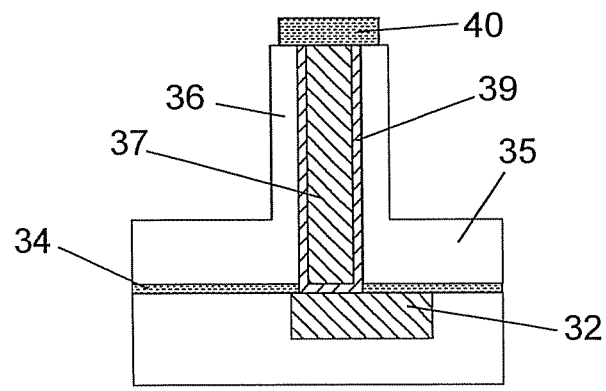
Figure 11H:
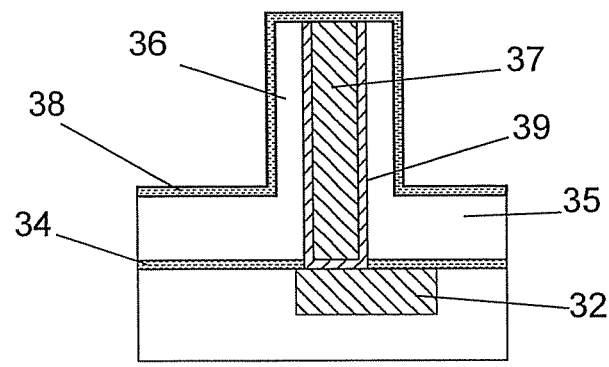
Figure 13A:
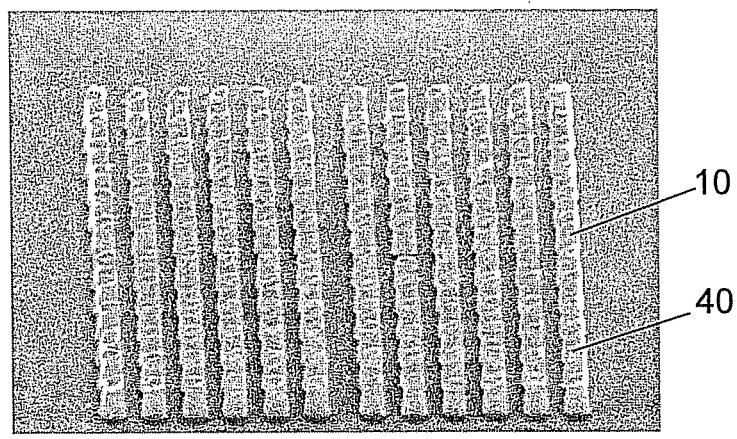
FIGS. 13 (i.e., 13(a) to 13(c)) shows SEM pictures of microneedles covered with a 75 nm thick layer of electroplated Au.
Figure 13B:
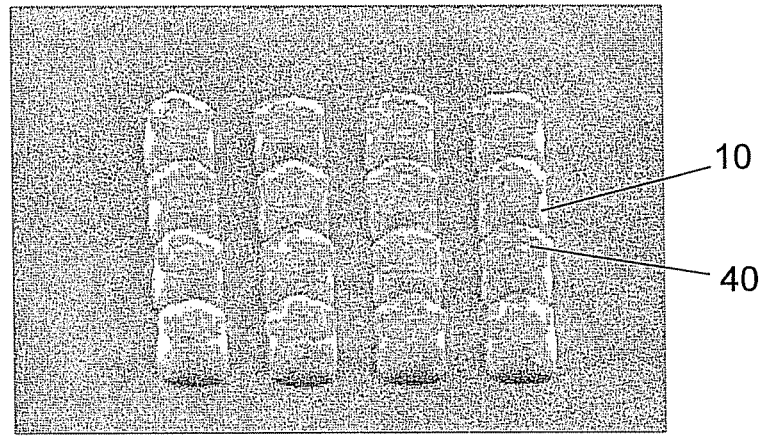
Figure 13C:
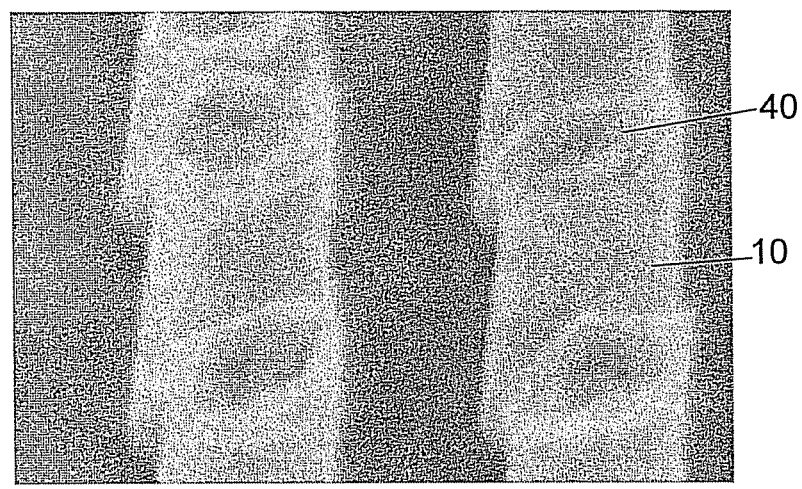

Finishing of the sensor as a passive electrode (as represented in FIGS. 10(b) and 11(h)) was done by electroplating 75 nm Au and patterning after the processing represented in FIG. 11(e). SEM pictures of the microneedles 10 are represented in FIG. 13(a) to 13(c). The microneedles 10 in FIG. 13(c) have a width of 250 nm at the top and 300 nm at the bottom. The length is 105 nm. Furthermore at the top of the microneedles 10, an electrode comprising 75 nm Au can be observed. FIG. 13(a) shows an array of microneedles 10 formed by the method as described above, each of the microneedles 10 comprising a Au electrode 40 on top. FIG. 13(b) shows another array of microneedles 10 comprising Au electrodes 40 on top and formed by the present experiment. FIG. 13(c) shows a detail of the array of microneedles 10 of FIG. 13(a).

Tungsten microneedles 10 with an aspect ratio (height/diameter) of 1, and thus with equal dimensions in height and diameter of approximately 1.5 µm, with a $SiO_2$ insulating layer and TiN top electrodes were produced as follows. The process was performed on top of Si wafers with a $SiO_2$ dielectric, but the process can also be performed on top of a wafer with metal contacts (for example Cu damascene or Al metal lines) in order to connect the nail electrode to, for example CMOS circuits.

First, a barrier layer of 50 nm SiC was deposited in order to prevent diffusion of toxic components from underlying circuitry 2 present in the substrate 1 to the conductive material 7 of the microneedle 10.

Subsequently, a dielectric layer of 3 µm $SiO_2$ was deposited. On the dielectric layer, a lithography step was performed prior to a DRIE-etch in order to etch holes through the 3 µm $SiO_2$ layer. The SiC was then removed with a second etch step.

Subsequently, Ti/TiN is deposited, resulting in a 10 nm/20 nm Ti/TiN layer at the sidewalls of the holes. This Ti/TiN layer will function as a diffusion barrier layer for the Tungsten. After this step, the holes were filled with tungsten by CVD (chemical vapour deposition).

In order to remove excess tungsten on top of the dielectric layer, the wafer was planarized with a CMP step, which exposes the 3 µm $SiO_2$ at the top, and leaving the holes filled with tungsten. Thereafter, a 100 nm layer of TiN was deposited, followed by a lithography step, leaving dots of resist centred on top of the tungsten-filled holes.

Figure 14:
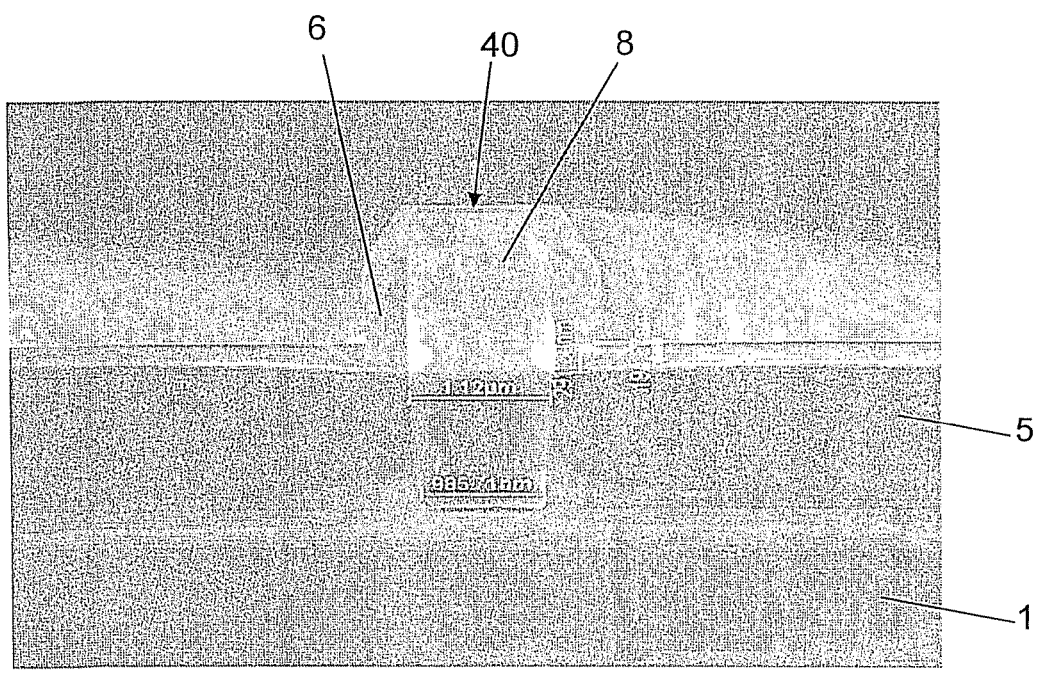
FIG. 14 shows a SEM picture of a tungsten needle with $SiO_2$ sidewalls and a TiN top electrode.

Subsequently, a DRIE etch step is performed to etch through the TiN and through the $SiO_2$. By correctly timing the DRIE etch, only the top 1.5 µm of $SiO_2$ is removed, which results in a remaining 1.5 µm of $SiO_2$ dielectric. Due to the shadow effect of the DRIE etch with the dot of resist, the $SiO_2$ under the resist is not removed, resulting in an insulating channel of $SiO_2$ and Ti/TiN around the tungsten core. This results in a structure as shown in FIG. 11(h) and is illustrated in FIG. 14 which shows a SEM picture of a microneedle structure 10 obtained by the experiment described above, i.e. a microneedle 10 comprising a tungsten filled channel 8 and $SiO_2$ insulating layer 6 surrounding the channel 8 and a TiN electrode 40 on top of the microneedle 10.

It is also possible to use, instead of tungsten, other materials as core material, such as for example: doped Si, SiGe, Al, Au, Pt, Cu, and the like, or other materials as top electrode, for example: Au, Pt, $SiO_2$, $Ta_2O_5$, and the like, or other materials as insulator: SiC, polymers, and the like.

It is to be understood that although preferred embodiments, specific constructions and configurations, as well as materials, have been discussed herein for devices according to the present invention, various changes or modifications in form and detail may be made without departing from the scope of this invention as defined by the appended claims.

The invention claimed is:

1. An electronic device for at least one of sensing and actuating, the electronic device comprising:
at least one microneedle on a substrate lying in a plane, wherein each of the at least one microneedle is perpendicular to the plane in which the substrate is lying, wherein each of the at least one microneedle comprises at least one channel surrounded by an insulating layer, the channel having a longitudinal axis which is directed in a direction substantially perpendicular to the plane in which the substrate is lying, wherein at least one microneedle comprises at least one channel that is at least partly filled with a filling material.

2. The electronic device according to claim 1, wherein the at least one channel that is at least partly filled with a filling material is completely filled with the filling material.

3. The electronic device according to claim 1, wherein at least one microneedle comprises at least one channel that is hollow.

4. The electronic device according to claim 1, wherein the filling material is a conductive material selected from the group consisting of Cu, Al, and W.

5. The electronic device according to claim 1, further comprising at least one active element or at least one passive element on top of at least one microneedle.

6. The electronic device according to claim 5, wherein the at least one active or the at least one passive element comprises a chip or electronic circuitry.

7. The electronic device according to claim 1, wherein the insulating layer has a thickness of between about 50 nm and about 1000 nm.

8. The electronic device according to claim 1, wherein the at least one microneedle has a diameter between about 100 nm and about 6 µm, a height between about 150 nm and about 50 µm, and an aspect ratio between about 0.5 and about 10.

9. The electronic device according to claim 1, further comprising at least two microneedles on the substrate, wherein a further insulating layer covers at least a part of the substrate and lies between the microneedles.

10. The electronic device according to claim 9, wherein either one or both of the insulating layer and the further insulating layer comprise at least one material that can serve as an electrical insulator or as a diffusion barrier.

11. The electronic device according to claim 9, wherein either one or both of the insulating layer and the further insulating layer comprise at least one material selected from the group consisting of silica, silicon carbide, and silicon nitride.

12. The electronic device according to claim 1, further comprising electronic circuitry in the substrate.

13. The electronic device according to claim 1, further comprising at least one microfluidic channel in the substrate.

14. The electronic device according to claim 1, wherein at least one microneedle comprises two channels, wherein each of the two channels is at least partly filled with the filling material, wherein the two channels are insulated from each other, and wherein each of the two channels is connected to a different electronic circuitry present in the substrate.

15. A method for manufacturing an electronic device for at least one of sensing and actuating, the method comprising:
   providing on a substrate lying in a plane at least one microneedle, wherein each of the at least one microneedle is perpendicular to the plane in which the substrate is lying, and wherein each of the at least one microneedle comprises at least one channel surrounded by an insulating layer, the channel having a longitudinal axis which is directed in a direction substantially perpendicular to the plane in which the substrate is lying, wherein providing on the substrate lying in the plane the at least one microneedle comprises (a) providing a patterned insulating layer on the substrate, the patterned insulating layer comprising at least one hole extending through the patterned insulating layer down to the substrate and (b) etching the patterned insulating layer to form an insulating layer that surrounds at least one cavity; and
   at least partly filling at least one of the at least one holes with a filling material.

16. The method according to claim 15, wherein the providing step is performed by using CMOS process technology.

17. The method according to claim 15, further comprising: providing at least one active element or at least one passive element on top of at least one microneedle.

18. The method according to claim 17, wherein the providing at least one active element or at least one passive element on top of at least one microneedle is performed by providing a layer of material, a chip, or electronic circuitry on top of the at least one microneedle.

19. The method according to claim 15, further comprising: fabricating electronic circuitry in the substrate.

20. The method according to claim 19, wherein the fabricating electronic circuitry in the substrate is performed by using CMOS process technology.

21. The method according to claim 15, further comprising: fabricating at least one microfluidic channel in the substrate.

22. An electronic device formed by the method of claim 15.

23. An electronic device for at least one of sensing and actuating, the electronic device comprising:
   at least one microneedle on a substrate lying in a plane, wherein each of the at least one microneedle is perpendicular to the plane in which the substrate is lying, wherein each of the at least one microneedle comprises at least one channel surrounded by an insulating layer, the channel having a longitudinal axis which is directed in a direction substantially perpendicular to the plane in which the substrate is lying, wherein the at least one channel comprises a plurality of channels.

* * * * *